(12) United States Patent
Travas-Sejdic et al.

(10) Patent No.: US 8,378,058 B2
(45) Date of Patent: Feb. 19, 2013

(54) CONDUCTING POLYMERS AND USES THEREOF

(75) Inventors: Jadranka Travas-Sejdic, Auckland (NZ); Christian Soeller, Auckland (NZ); Hui Peng, Auckland (NZ); Vittorio Capno, Auckland Central (NZ); Ralph Cooney, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 859 days.

(21) Appl. No.: 12/063,221

(22) PCT Filed: Aug. 11, 2006

(86) PCT No.: PCT/NZ2006/000207
§ 371 (c)(1),
(2), (4) Date: Apr. 14, 2009

(87) PCT Pub. No.: WO2007/018439
PCT Pub. Date: Feb. 15, 2007

(65) Prior Publication Data
US 2009/0215958 A1 Aug. 27, 2009

(30) Foreign Application Priority Data
Aug. 11, 2005 (NZ) .......................... 541788

(51) Int. Cl.
C08G 69/10 (2006.01)

(52) U.S. Cl. .................. 528/328; 536/22.1; 536/25.3
(58) Field of Classification Search ............... 536/22.1, 536/25.3; 528/328
See application file for complete search history.

(56) References Cited

U.S. PATENT DOCUMENTS

| | | | |
|---|---|---|---|
| 5,254,627 A * | 10/1993 | Rossi et al. ............ | 525/203 |
| 5,420,237 A | 5/1995 | Zemel | |
| 5,837,859 A * | 11/1998 | Teoule et al. ........... | 536/25.3 |
| 6,160,103 A * | 12/2000 | Marchand et al. ....... | 536/23.1 |
| 6,187,914 B1 * | 2/2001 | Teoule et al. ........... | 536/25.3 |
| 6,197,949 B1 * | 3/2001 | Teoule et al. ........... | 536/25.3 |
| 6,380,346 B1 | 4/2002 | Han | |
| 7,842,820 B2 * | 11/2010 | Maier et al. ............ | 548/542 |
| 2002/0081275 A1 | 6/2002 | Han | |
| 2005/0224765 A1 * | 10/2005 | Hsu et al. ............. | 252/500 |

FOREIGN PATENT DOCUMENTS

| | | |
|---|---|---|
| WO | 97/21228 | 6/1997 |
| WO | 98/52042 | 11/1998 |
| WO | 01/05863 | 1/2001 |
| WO | 03/062790 | 7/2003 |
| WO | WO 2004067533 A1 * | 8/2004 |
| WO | 2005/100600 | 10/2005 |
| WO | 2006/084088 | 8/2006 |

* cited by examiner

Primary Examiner — James J Seidleck
Assistant Examiner — Peter A Salamon
(74) Attorney, Agent, or Firm — Occhiuti Rohlicek & Tsao LLP

(57) ABSTRACT

A conducting polymer including a conducting linker to connect a probe to the polymer, the linker including an unsaturated organic chain.

26 Claims, 16 Drawing Sheets

CONDUCTING POLYMERS AND USES THEREOF

This application is the National Stage of International Application No. PCT/NZ2006/000207, filed on Aug. 11, 2006, which claims the benefit of New Zealand Application Serial No. 541788, filed on Aug. 11, 2005. The contents of both of the foregoing applications are hereby incorporated by reference in their entirety.

TECHNICAL FIELD OF THE INVENTION

The present invention broadly relates to conducting polymers including a conducting linker which connects a probe to the polymer.

BACKGROUND

The electronic changes which occur in chemical or biological molecules when interacting with other molecules provide a sensitive and convenient method of studying molecule/molecule association. For example, technology capable of recording the electronic changes which occur in specific DNA/RNA sequences has been of great importance in numerous applications, such as in medical research and clinical diagnosis.

In general, DNA/RNA array sensors are based on single-stranded oligonucleotide (ODN) probes (of known sequence) immobilised on a physical substrate.

Addition of tagged ODNs in the sample may result in immobilisation of tagged ODNs via Watson-Crick base pairing (or hybridization) if the sequences are complementary. The resulting double stranded ODN is immobile, being anchored by the probe, as well as tagged by prior sample tagging.

The immobilisation of tagged ODNs provides the basis of sample detection and the resulting pattern is detected by (for example) fluorescence or chemiluminescences from the tag. The main disadvantages of such detection methods are cost, complexity and inefficiency of tagging reactions.

A number of alternative 'label-free' methodologies have also been developed, such as acoustic (Okahata et al., 1992; Ma, et al., 2002), optical (Piunno et al., 1994; Isola et al., 1998) and electrochemical (XU et al., 2000; Wang et al., 2001, 2003; Hashimoto et al., 1994; Napier et al., 1997; Pividori et al., 2000) methods which seek to detect the hybridization event directly. Electrochemical approaches using metal complexes (Takenaka et al., 2000), organic redox indicators (Millan et al., 1993) or nano particles (Wang et al., 2001, 2003) have also been investigated for their suitability to report hybridization.

Conducting polymers are attractive substrates for nucleotide sensors as they can act as an electronic transducer for charged species binding to their surface, and several methods for the immobilisation of ODN probes onto conducting polymers have been reported. In addition, the rich chemistry associated with fabrication of conducting polymer sensors and electrodes allows the detection of a broad range of chemical or biological materials according to the selection of probe and the capacity of the conducting polymer to bind the probe (Janata & Josowicz, 2003; Saxena & Malhotra, 2003).

Initial approaches to construct conducting polymer ODN sensors included direct adsorption of the ODN probes onto oxidized polypyrrole (PPy) films by electrostatic attractions (Palecek, 2002; Minehan et al., 1994) or incorporation of the ODN probe into the polymer film as a macro-counterion (Wang et al., 1999). However, these methods constrain the orientation of the ODN probe resulting in high steric and kinetic barriers to hybridization, and the possibility of oxidative damage to the ODN probes. The result is that such methods have poor sensory properties.

To overcome steric constraints, several groups have electro copolymerised N-position substituted pyrroles with pyrrole to functionalise the polymer for ODN probe linkage to the substrate (Wang et al., 2000; Livache et al., 1995; Lassalle et al., 2001). However, the resulting poly(N-substituted pyrrole) possessed lower conductivity, possibly due to a lack of ring planarity in the resulting polymer.

Of most interest has been a report that a 3-substituted pyrroles gave rise to a polymer film with higher conductivity (Delabouglise et al., 1989). A probe may be chemically coupled to a polymer by an amino-modified ODN.

U.S. Pat. No. 6,096,825 discloses such a conducting polymer formed from a 3-substituted polypyrrole polymer. The conducting polymer includes a linker unit located in the 3-position of pyrrole monomers. The linker is bound to the pyrrole, at one end, and to the probe at the other end.

The linker connecting the probe to the polymer represents a key feature in electrochemical transduction between the probe and the polymer. Typically short saturated organic chains of 2- to 4-carbon atoms have been used to connect the probe to the polymer (see also H. Peng et al *Label-free electrochemical DNA sensor based on functionalised conducting polymer* Biosensor and Bioelectronics 20 (2005) 1821-1828).

There is a continuing need to synthesize new conducting polymers, and in particular linkers which enhance or improve electronic transduction between the probe and the polymer backbone. In addition, there is a continuing need to provide conducting polymers which have negligible effect on the chemical or biological sensory properties of probes they are attached to.

Throughout this specification reference is made to "unsaturated" or "conjugated" organic chains. The words "unsaturated" and "conjugate" refer to double or triple bonds between two or more atoms. The words are used interchangeably throughout the specification.

Throughout the specification reference is made to "probes". The use of the word "probe" in this specification is intended to be interpreted inclusively and including any chemical or biological species which may be tethered via a linker to a polymer backbone. A probe may include a single or double stranded ODN, a virus, a protein, a cell, a peptide nucleic acid (PNA), a polysaccharide, a drug, or an RNA, for example.

Throughout the specification reference is made to the phrase "sensory properties" in relation to a probe interaction with other chemical or biological molecules or species. Sensory properties should be interpreted as the ability of the probe to hybridize and/or otherwise interact through non-covalent bonding or the like with another chemical or biological molecules or species and to be efficiently transduced into a useful signal. Ideally a biological probe, for example, which is bound to a conducting polymer as far as possible, retains its natural sensory properties.

OBJECT OF THE INVENTION

It is an object of the present invention to provide a conducting polymer which overcomes or ameliorates at least one of the abovementioned disadvantages and/or at least provides the public with a useful choice.

SUMMARY OF THE INVENTION

According to one aspect of the invention there is provided a conducting polymer including a conducting linker to connect a probe to the polymer, the linker including an unsaturated organic chain.

Preferably the linker is adapted to locate the probe at a predetermined distance from remaining portions of the polymer thereby optimising sensory properties of the probe.

Preferably the linker has a predetermined range of orientations brought about by unsaturated bonds.

Preferably the linker is of the general formula I, II, II or IV:

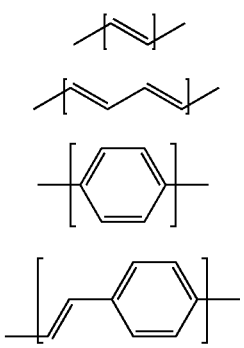

(I)
(II)
(III)
(IV)

Preferably the linker extends from at least one monomer of the polymer.

Preferably the polymer is a polypyrrole, polythiophene, polyaniline, poly(p-phenylene vinylene) or poly(p-phenylene) polymer.

According to a further aspect of this invention there is provided a functionalised monomer of the general formula V:

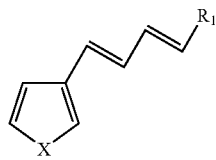

(V)

wherein X is N, S or C and $R_1$ is —$NH_2$, —$CO_2H$, —COH, —OH or N-hydroxyphthalimide.

One preferred form of the compound is 5-(1H-pyrrol-3-yl) 2,4-pentadienoic acid (PPDA).

According to a further aspect of this invention there is provided a conducting polymer including at least one functionalised monomer of the general formula VI:

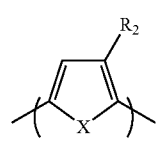

(VI)

wherein X is N, S or O, and $R_2$ is an unsaturated organic chain.

Preferably, $R_2$ is adapted to engage with a probe from the free end.

Preferably $R_2$ is of a general formula I to IV and provides a functional group at the free end.

Preferably, the functional group is —$NH_2$, —$CO_2H$, —COH, —OH or N-hydroxyphthalimide.

Preferably the conducting polymer may be formed from the polymerisation or co-polymerisation of the functionalised monomer.

Preferably the conducting polymer is formed from co-polymerisation of the functionalised monomer with an unsubstituted or non-functionalised monomer.

Preferably the co-polymerisation involves a ratio of non-functionalised to functionalised monomers of 10000:1 to 1:1.

Preferably the unsubstituted or non-functionalised monomer may be pyrrole or thiophene.

According to a further aspect of this invention there is provided a use of a functionalised monomer of the general formula VII in the construction of a conducting polymer:

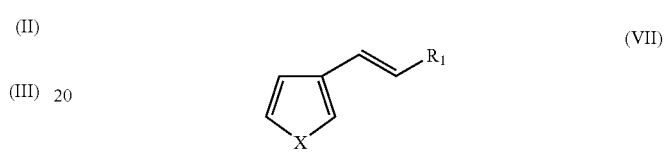

(VII)

wherein X is N, S or O, and $R_1$ is a functional group.

Preferably the functional group is —$NH_2$, —$CO_2H$, —COH, —OH or N-hydroxyphthalimide.

According to a further aspect of this invention there is provided a functionalised monomer of the general formula VIII:

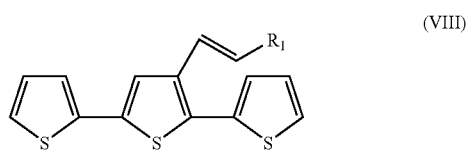

(VIII)

wherein $R_1$ is —$NH_2$, —$CO_2H$, —COH, —H or N-hydroxyphthalimide.

According to a further aspect of this invention there is provided a use of a functionalised monomer of the general formulas V, VII or VIII in the construction of a conducting polymer.

Preferably the conducting polymer includes functionalised and non-functionalised monomers.

Preferably the functionalised monomers includes copolymerised functionalised monomers.

Preferably the ratio of non-functionalised monomers to copolymerised functionalised monomers is between about 80:1 and about 1:1.

According to a further aspect of this invention there is provided a conducting linker connecting a probe to a conducting polymer, the linker including an unsaturated organic chain.

According to a further aspect of this invention there is provided a conducting polymer substantially as herein described with reference to the Figures.

According to a further aspect of the invention there is provided a functionalised monomer substantially as herein described with reference to the Figures.

According to a further aspect of the invention there is provided a use of a functionalised monomer substantially as herein described with reference to the Figures.

According to a further aspect of this invention there is provided a conducting linker substantially as herein described with reference to the Figures.

According to a further aspect of this invention, there is provided a method of reducing charge transfer resistance between a conducting polymer and a probe, the method including the steps of connecting the conducting polymer to the probe via a linker constructed of an unsaturated organic chain.

Preferably the linker is selected from any one of the groups of general formula I, II, III, or IV.

According to a further aspect of the invention, there is provided a method of preparing a conducting polymer including the steps of carrying out polymerisation of polymer monomers in a solvent of $LiClO_4$ in acetonitrile or propylene carbonate (PC).

DESCRIPTION OF THE FIGURES

The present invention will now be described by way of example and with reference to the Figures. Brief descriptions of the Figures are provided below.

DESCRIPTION OF A PREFERRED EMBODIMENT

Figure 1:
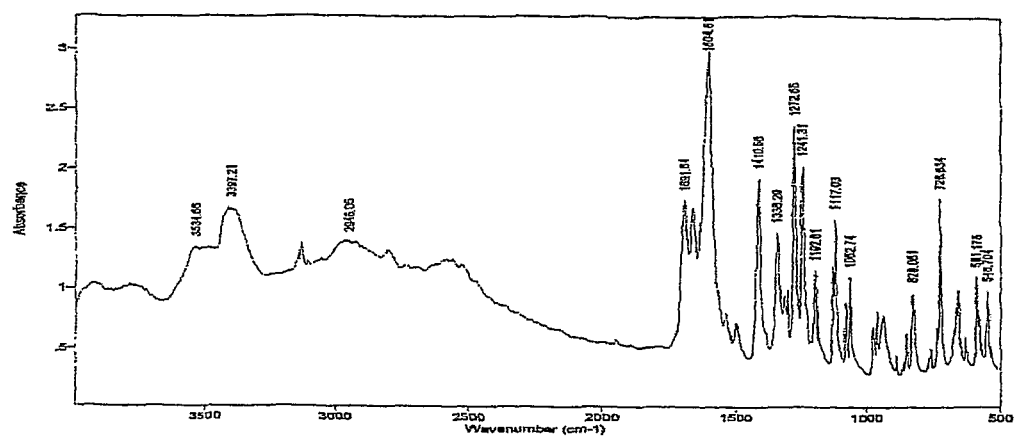
FIG. 1 IR spectra of 3-(3-pyrrolyl)acrylic acid.

Accurate and fast detection of biological material is becoming increasingly important in a number of fields such as biomedical research, clinical diagnosis, forensics and food quality. Examples include identification of genetic mutations and early detection of pathogens.

The present invention provides a new series of conducting polymers including conducting linkers which in use connect a probe to the polymer backbone. The probe may include a biological species under study (e.g. DNA and RNA sequences, proteins etc).

The linker part of the conducting polymer is adapted to connect the probe to the polymer backbone such that electronic conductivity between the probe and polymer is maintained and enhanced.

The inventors have discovered that the charge transfer resistance of a conducting polymer can be decreased if the linker connecting the probe to the polymer backbone is an unsaturated organic chain. This means that an unsaturated organic chain linker provides an improved linker for connecting the probe to the conducting polymer backbone over currently used linkers.

This discovery opens the way for the construction of linkers which improve electronic pathways between the probe (or sensory recognition site) and the polymer backbone even when the linker may be relatively long (greater than 4 atoms in length). A linker may be for example up to 17 atoms or more in length provided that the organic chain is conjugated.

This discovery also allows linkers to be constructed that locate the probe at a predetermined distance from the conducting polymer to optimise sensory properties of a particular probe while retaining electrical transduction between the probe and the polymer. Thus electronic transduction can be maintained even when the probe may be located some distance from the conducting polymer.

There are also other advantages that an unsaturated organic linker provides. Unsaturated bonds are more mechanically stiff. This means that an unsaturated organic linker has improved orientational control over the probe in use. For example, the likelihood that the probe is directed outwardly from the conducting polymer backbone and in an orientation capable of facilitating sensory events, such as interactions or hybridization with other chemical or biological molecules, is greater when the probe is spaced by a mechanically stiff unsaturated organic linker.

In contrast a saturated linker can allow a probe to swivel in toward the conducting polymer and prevent, reduce and hinder sensory interaction with other chemical or biological molecules. Thus the present invention also allows the location and/or orientation of the probe to be predetermined by the selection of particular unsaturated molecules to provide the linker.

The linker may include a variety of unsaturated or conjugated organic molecules of at least more than 2 carbons in length. The linker could include species such as alkenes, alkynes, conjugated heterocycles (such as substituted pyridine, pyrroles, thiophene rings and the like), substituted benzene rings (such as phenyl, biphenyl rings and the like), branched and linear unsaturated organic chains, halo-substituted alkenes and halo-substituted alkynes. Those skilled in the art will be aware of other unsaturated organic species which could be used to provide a linker, in view of the teaching of this application.

In one preferred embodiment the linker of the present invention may include an unsaturated organic chain of the general formula I or the general formula II:

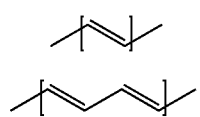

(I)

(II)

The linker is connected in use at one end to the polymer backbone and at the other end to the probe. The linker of general formula I illustrates the simplest unsaturated unit which may act as a linker.

Other linkers may include organic chains of general formula (III) and (IV).

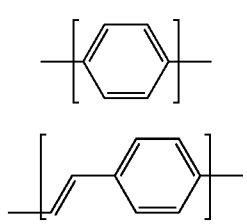

(III)

(IV)

As mentioned above, the linker may include 17 atoms or more in length, provided that conjugation is maintained along the length of the linker. Of course, it will be appreciated that the longer the linker, the less steric hindrances there may be for the probe-target complex formation, but the longer the linker is the higher chances of electron transfer hindrance at the electroactive film surface. In addition, longer linkers may cause steric hindrance during the polymerization of the (co) polymer. An optimum length for a simple linear linker may be around 3 to 9 atoms in length. However it will be appreciated that the optimum length of linker will vary depending on the linker species.

The use of conjugated ring units within the linker such as shown in general formulas III and IV can be used to improve steric positioning of the probe relative to the polymer backbone. In addition the rings may improve predictability of the position of the probe spatially. Thus the linker may be tailored to the particular requirement of the probe.

Examples 1 and 4 illustrates that a 3 carbon unsaturated linker of the present invention has good electronic transduction between the polymer and the probe. Example 2 illustrates that a 5 carbon unsaturated linker has significantly improved electrical conduction over the equivalent saturated 5 carbon linker (of Example 3).

When an unsaturated organic linker connects a probe to a polymer, the changes in the AC impedance spectra expressed through charge transfer resistance values ($R_{ct}$) observed in sensory experiments, are much more sensitive to perturbations caused by the probe hybridizing with another biological species. The stronger change in $R^{ct}$ (taken as the index of the sensor response) implies the better sensor properties. The change in $R_{ct}$ is stronger when unsaturated organic linkers are used in contrast to their equivalent saturated linkers.

Not wishing to be bound by a specific hypothesis, the inventors believe that unsaturated organic linkers provide improved electronic transduction because there is greater p orbital overlap along an unsaturated or conjugated organic chain system.

Previous saturated organic linkers had to be short (of about 2 to 5 atoms in length) in order to maintain electronic transduction between the probe and the polymer. If the saturated chain was long (of about 5 or more atoms long), electronic transduction was substantially diminished. Thus linkers of relatively short length were typically used; of about 2 to 4 carbon atoms in length.

The improved linkers identified, and herein described, have allowed the construction of enhanced conducting polymers-based sensors. The conducting polymer includes a linker unit bound to a monomer of the conducting polymer backbone. Once construction of the conducting polymer is complete, the linker(s) may be covalently coupled to a probe and sensory experiments conducted.

In a preferred embodiment the conducting polymer includes at least one functionalised monomer of the general formula VI:

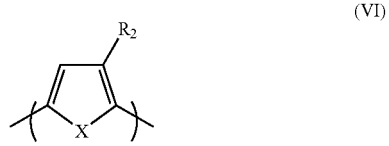

(VI)

wherein X is N, S or O, and $R_2$ is an unsaturated organic chain. $R_2$ represents the linker unit, for examples, an unsaturated organic linker of the general formula (I) to (IV). "Functionalised monomers" are used to define substituted monomers, or monomers having the linker unit. A preferred form of the compound is 5-(1H-pyrrol-3g1)2; 4-pentadienoic acid (PPDA) (see Example 2). The conducting polymer may be prepared by copolymerisation of functionalised monomers and non-functionalised monomers. Non-functionalised monomers may include unsubstituted monomers or monomers without a specific linker group.

In a further preferred embodiment X is N (resulting in a poly(3-substituted pyrrole), see Example 1 to 3) or S (resulting in a poly (3-substituted thiophene), see Example 4). At one free end of $R_2$ is a functional group adapted to connect the conducting polymer to a probe. The functional group may include —$NH_2$, —COH, —$CO_2H$, —OH, N-hydroxyphthalimide but may also include other functional entities, such as —SH, biotin or avidin.

Examples of functionalised monomers include species of the general formula V and VII.

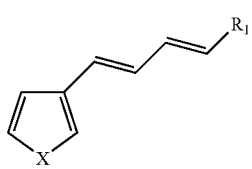

(V)

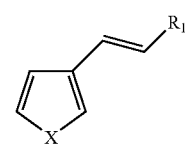

(VII)

Wherein $R_1$ is a functional group and may include for example —$NH_2$, —COH, —$CO_2H$, —OH, N-hydroxyphthalimide or another functional group.

A functionalised monomer is not restricted to a single pyrrole or thiophene unit coupled to a linker. Example 4 illustrates a functionalised monomer of the general formula VIII having three thiophene units and one linker. One thiophene unit provides the linker.

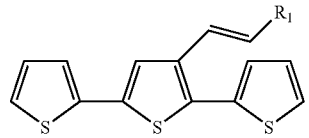

(VIII)

wherein $R_1$ is —$NH_2$, —$CO_2H$, —COH, —OH, N-hydroxyphthalimide or another functional group.

A variety of conducting polymer backbones may be suitable including polypyrrole, polythiophene, polyaniline, poly(p-phenylene vinylene) or poly(p-phenylene) polymer. Functionalised monomers may be prepared from monomers of these polymers.

The invention also provides a method of constructing a conducting polymer. The conducting polymer is constructed by homopolymerisation with functionalised monomers or copolymerisation with functionalised monomers and non-functionalised monomers.

A conducting polymer which has a linker of the general formula I and II, may be constructed by homopolymerisation or copolymerisation with a functionalised monomer of the general formula V, VII or VIII for example.

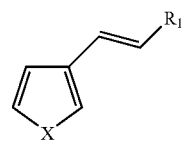

(VII)

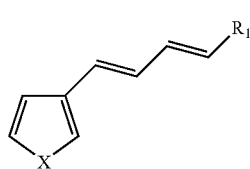

(V)

where X includes N, S or O; or

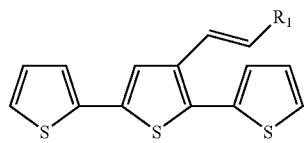

(VIII)

and where $R_1$ includes —$CO_2H$, —COH, —$NH_3$, —OH, N-hydroxyphthalimide or any other suitable functional group.

The synthesis of functionalised monomers of general formulas V, VII, and VIII are discussed in Examples 1, 2 and 4 respectively.

Following synthesis, the functionalised monomers may be homopolymerised with like monomers to provide the conducting polymer. Alternatively, the functionalised monomer may be copolymerised with non-functionalised monomers such as pyrrole, thiophene or the like to form the conducting polymer. Thus another aspect of the invention is a use of a functionalised monomer herein described to construct conducting polymers.

In practice polymerisation occurs on the surface of an electrode. The conducting polymer forms as a film on the electrode surface. Typically the electrode may be of gold, platinum, glassy carbon, or stainless steel. The electrode is placed in solvent in the presence of the functionalised monomer, and the non-functionalised monomer if a copolymer of conductive polymer is to be prepared. It will be appreciated that the non-functionalised monomer does not have to be an equivalent monomer unit as the functionalised monomer. For example a functionalised pyrrole monomer could be polymerised with a non-functionalised thiophene monomer.

The inventors have found that the choice of polymerising solvent has an effect on the properties of the sensor obtained. Organic solvent-based electrolytes such as $LiClO_4$ in acetonitrile or propylene carbonate (PC), gives significantly better films than aqueous based electrolytes. The use of PC, in particular, leads to films of conductor polymers with superior electrochemical characteristics.

If the functionalised monomers are copolymerised, the ratio of non-functionalised monomer to functionalised monomer is preferably in the range from about 10000:1 to 1:1, and more preferably below about 80:1. However, the inventors have found that when the concentration of functionalised monomers is increased beyond about 50:1 the properties of conducting polymer film formed on the electrode begin to decrease.

Once the conducting polymer is prepared, the probe may be connected to it via the linker. This subsequently allows studies of the sensory probe to be undertaken. Typically this involves removing the electrode having the conducting polymer film from the solvent and placing the electrode in a solution containing the probe. Preferably the probe is chemically and/or covalently bound to a free end of the linker group.

A functional group on the free end of the linker may include —$CO_2H$, —CHO, —$NH_3$, —OH or N-hydroxyphthalimide which allows the linker to be connected to the probe. These functional groups are most desirable at the end as they allow simple chemistry to connect the linker to the probe. However, it will be appreciated that a variety of other functional groups could be provided at the linker end, for example —SH, biotin or avidin.

In an alternative embodiment the probe may form a strong physical bond to the linker group otherwise than by a covalent bond.

The probe may include a variety of biological species, including an ODN, a virus, a drug, a polysaccharide, a protein, a cell, an RNA or the like. However, the probe is not limited specifically to a biological species and may include any chemical compound which must be affixed to a solid support. It will be appreciated that the probe is not essential to the overall workings of the invention.

Once the probe is coupled to the conducting polymer sensory experiments (or hybridization experiments) may be conducted to study the sensory properties of the probe.

The conducting polymers of the present invention may have a variety of commercial uses. As discussed throughout the specification, the conducting polymers of the present invention may be connected via the linker to a probe, where it is desirable to study the properties of the probe. Where the probe is a protein, for example, the conducting polymer may be used to study protein/protein interactions so that scientists may develop a greater understanding of their interaction in nature. This may allow the development of new drugs.

Alternatively a drug may be connected to the conducting polymer so that its physical interaction with a target protein can be studied.

Where the probe is an ODN, the conducting polymer may be used to isolate a complementary sequence or gene on a solid conducting polymer film support which may later be isolated. This is just a few examples of commercial applications of the present invention.

A further aspect of the invention includes the selection of a linker which optimises the sensory properties of the probe. It will be appreciated that the sensory properties of the probe may be affected by electrostatic interaction between the structure/groups of the probe and the structure/groups making up the linker. It should therefore be understood that the invention provides a method of enhancing the sensory properties of the probe, including the steps of selecting a linker of optimum length and consisting of groups which substantially avoid electrostatic attraction/interaction with groups on the probe. In this way the sensory properties of the probe during hybridization events can be studied effectively.

The invention will now be described by reference to the Examples.

EXAMPLE 1

Synthesis of Functionalised Monomers of the General Formula VII (3-pyrrolyl)acrylic acid, its (Co)Polymer and the Evaluation as a DNA Sensor (a) Synthesis (3-pyrrolyl)acrylic acid 5 was synthesized as outlined in the Scheme I.

Scheme I: Synthesis of a functionalised monomer of the general formula III (3-pyrrolyl)acrylic acid (PAA)

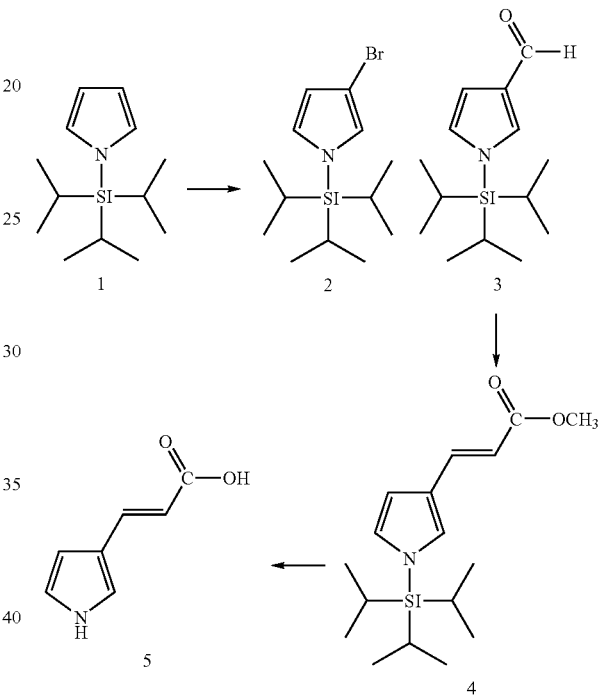

Synthesis procedure was as follows:

N-(Triisopropylsilyl)pyrrole (1)

Pyrrole (1.0 mL, 0.96 g, 15 mmol) was added dropwise at 0° C. to a stirred suspension of sodium hydride (0.758 g of 50% dispersion in mineral oil, 16 mmol) in anhydrous DMF (20 mL). When hydrogen evolution (foaming) had ceased, triisopropylsilyl chloride (3.1 mL, 2.8 g, 15 mmol) was added dropwise and stirring at 0° C. was then continued for 0.75 h. The reaction mixture was partitioned between ether and water, and the ether phase was washed with water, dried over sodium sulfate, and evaporated in vacuum. Purification by column chromatography on silica gel (hexane/ethyl acetate=10:1) gave an oil (1.01 g, 30.2% yield); $^1$H NMR ($CDCl_3$) δ 1.09 (d, 18 H, Me), 1.45 (sept, 3 H, CH), 6.31 (t, 2H, H-3.4), 6.80 (t, 2H, H-2.5). MS (M+H) m/z 224.

3-Bromo-1-(triisopropylsilyl)pyrrole (2)

NBS (N-bromosuccinimide; 0.8 g, 4.5 mmol) was added to a stirred solution of N-(triisopropylsilyl)pyrrole (1.0 g, 4.5 mmol) in anhydrous THF (10 mL) at −78° C. The reaction mixture was kept at −78° C. for 1-2 h and then left to reach room temperature (ca. 1 h). Pyridine (0.1 mL) and hexane (10 mL) were added, the resulting suspension was filtered through a plug of neutral alumina, and the filtrate was evaporated in vacuum. Purification by column chromatography on silica gel (hexane/ethyl acetate=10:1) gave oil (1.22 g, 90.1% yield). $^1$H NMR (CDCl$_3$) δ 6 1.08 (d, 18 H, Hz, Me), 1.42 (sept, 3 H, CH), 6.26 (dd, 1H, H-4), 6.66 (t, 1 H, H-5), 6.72 (dd, 1H, H-2). MS (M+H) m/z 302.

I-(Triisopropylsilyl)pyrrole-3-carboxaldehyde (3)

A solution of 1.6 M n-butyllithium in hexane (1.56 mL, 2.5 mmol) was added, at −78° C., to a solution of 3-bromo-1-(triisopropylsilyl)pyrrole (0.76 g, 2.5 mmol) in anhydrous THF (20 mL). After 15 min at −78° C., DMF (2.5 mmol) was added and 15 min thereafter the reaction was removed from the cooling bath and left to come to room temperature. The reaction mixture was quenched with water and extracted with ether. The extract was dried (MgSO$_4$,) and evaporated in vacuum. The residue was then purified by column chromatography on silica gel (hexane/ethyl acetate=7:3) and gave an oil (0.501 g, yield 80%). $^1$H NMR (CDCl$_3$) δ 1.10 (d, 18 H, Me), 1.47 (sept, 3 H, CH), 6.74 (m, 1 H, H-4), 6.77 (m, 1 H, H-5), 7.39 (dd, 1H, H-2), 9.82 (m, 1 H, CHO). MS (M+H) m/z 252.

3-(I-(Triisopropylsilyl)pyrrol-3-yl)-acrylic acid methyl ester (4)

(Triphenylphosphoranylidene) methyl acetate (3 mmol, 1.05 g, 1.5 equiv) was added to a solution of I-(Triisopropylsilyl)pyrrole-3-carboxaldehyde (0.502 g, 2.0 mmol) in anhydrous THF (20 mL). The reaction mixture was stirred at 30° C. for 2 h and concentrated in vacuum to give an oily residue, which upon purification by column chromatography on silica gel (hexane/ethyl acetate=10:1) gave the product 4.
$^1$H NMR (CDCl$_3$) 5 MS (M+H) m/z 308.

(3-pyrrolyl)acrylic acid (5) (PAA; General formula VIII)

3-(I-(Triisopropylsilyl)pyrrol-3-yl)-acrylic acid methyl ester (3 mmol, 0.924 g,) was added to a solution of 10% NaOH (6 mL) and methanol (3 mL). The mixture was refluxed for 2 h. Methanol was removed by distillation in vacuum and the aqueous solution was adjusted to pH 4.3 with 10% HCl. The resultant precipitate was collected, washed with cold water, and re-crystallized from ethanol-hexane mixture to give 5. IR (KBr) 3397 s, 2200-3500 br., 1691 m, 1604 s.
$^1$H NMR ((CH$_3$)SO-d$_6$) δ 5.95 (d, 1H, —CH=CHCO—), 6.40 (m, 1H), 6.80 (m, 1H), 7.18 (m, 1H), 7.46 (d, 1H, —CH=CHCO—), 11.15 (s, 1H), 11.80 (s, 1H).

Figure 2:
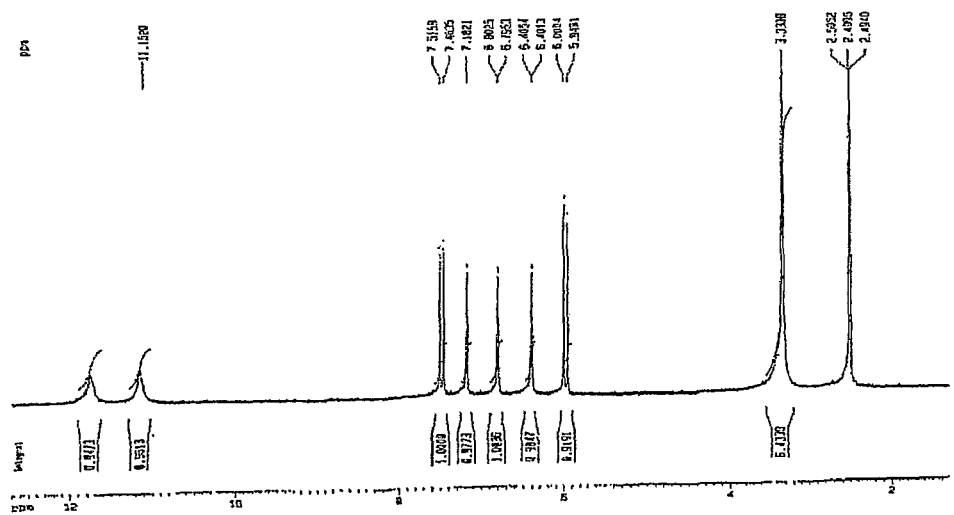
FIG. 2 $^1$H NMR spectra of 3-(3-pyrrolyl)acrylic acid.
Figure 3:
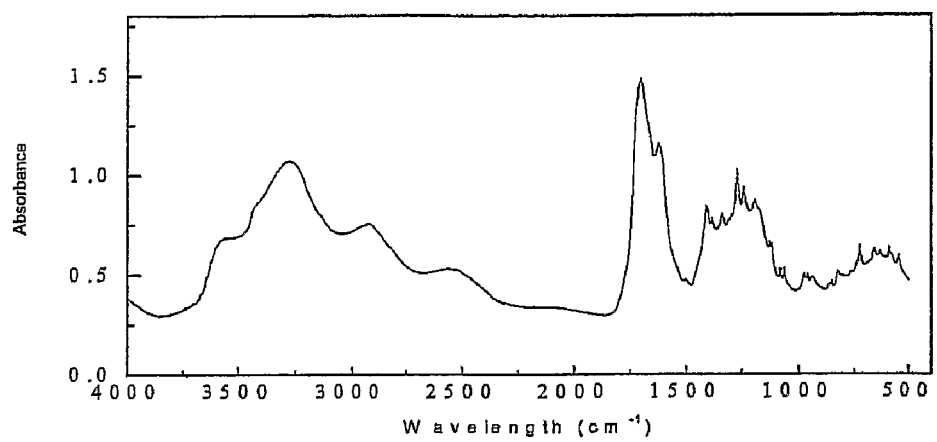
FIG. 3 IR spectra of chemically polymerised poly(PAA).
Figure 4:
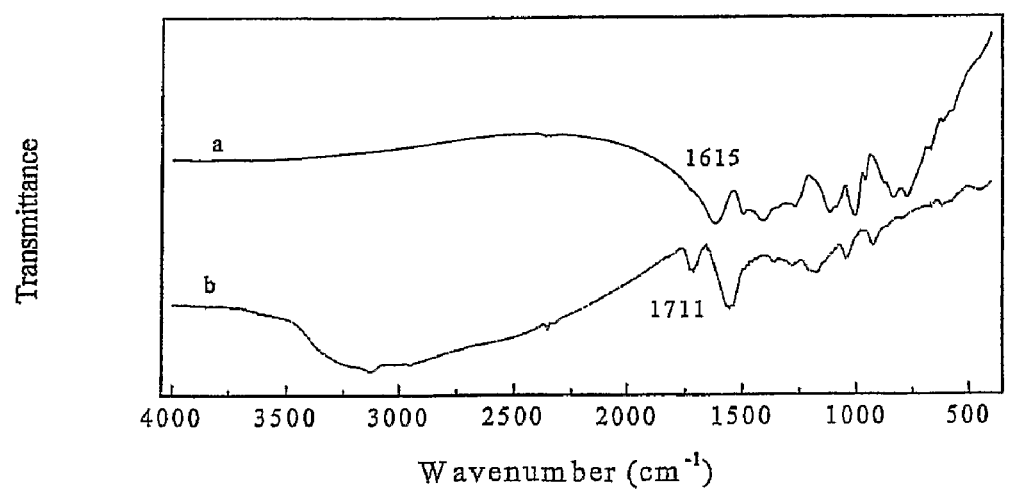
FIG. 4 FTIR spectra of polypyrrole (a) and poly(Py-co-PAA) (b).
Figure 5:
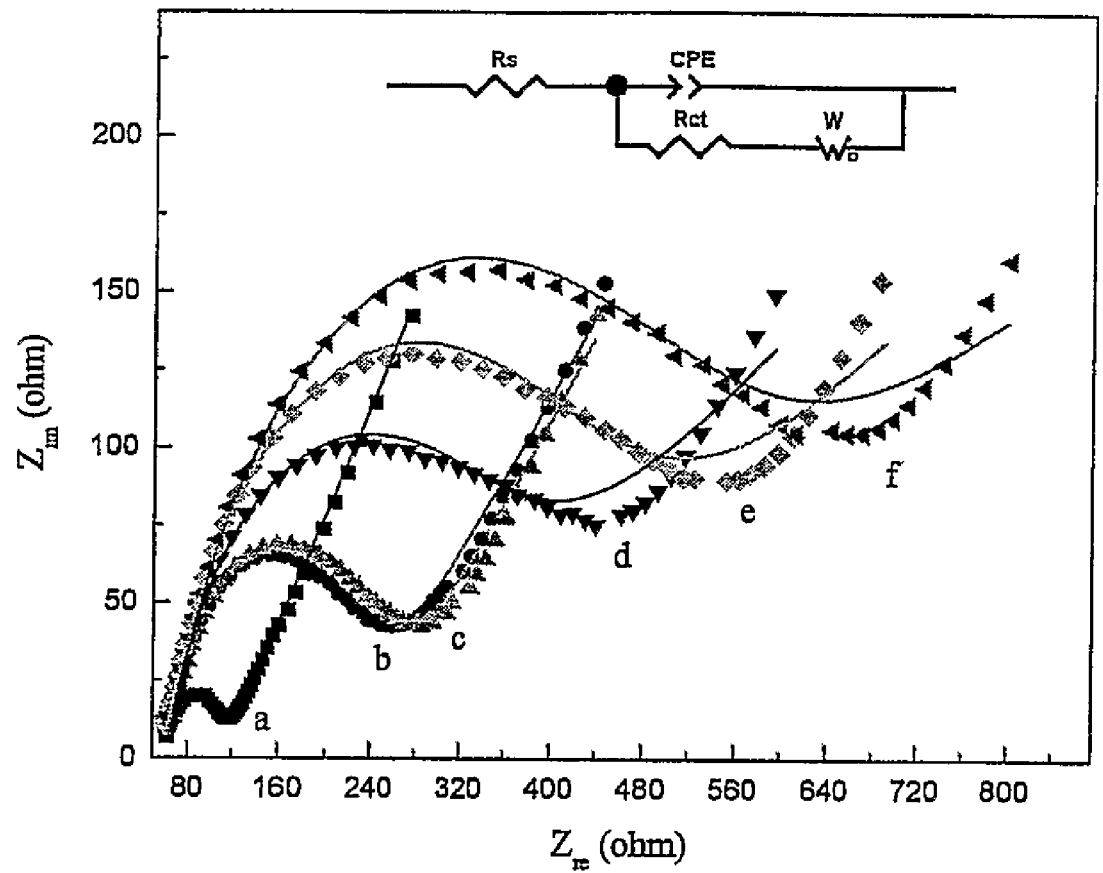
FIG. 5 Nyquist plots (-Zim vs Zre) for electrochemical impedance measurement based on electrodes coated with poly(Py-co-PAA) in PBS solution (pH 7.4) containing 5.0 mM $Fe(CN)_6^{3-}/Fe(CN)_6^{4-}$ before immobilisation of the ODN probes (a); after immobilisation of ODN probes (b); after hybridization with 2 nM (c), 20 nM (d), 200 nM (e) and 2 μM (f) complementary ODNs. In all cases, the experimental data are shown as symbols and the fitting data as solid lines.

The FTIR spectra and $^1$H NMR spectra of (3-pyrrolyl)acrylic acid are presented on FIGS. 1 and 2.
(b) Chemical Polymerisation of PAA
0.20 g ammonium persulfate was added to PAA solution (0.30 g) and the mixture was stirred for 5 h. The precipitate was collected and washed with acetone and water. FIG. 3 presents FTIR spectra of the polymer.
(c) Electrocopolymerisation of the Poly (Py-co-PAA) Copolymer The electrochemical synthesis of poly(Py-co-PAA) films was carried out by using CH Instrument electrochemical workstation (Model 440, CH Instruments, USA) at a fixed potential of 1.0 V (Ag/AgCl,). A three-electrode cell with a volume of 3.0 mL, comprising a glassy carbon working electrode (BAS, 3.0 mm in diameter), an Ag/AgCl (3M KCl) reference electrode and Pt wire counter electrode, was used. Prior to electropolymerisation, glassy carbon electrodes were polished with a 0.5 μm alumina slurry (Allied Tech Products, Inc, USA), then washed with acetone, ethanol and Milli-Q water. The polymerisation solution contains 0.5 M Py, 6.25 mM PAA, and 0.2 M LiClO$_4$ in 2 mL acetonitrile or propylene carbonate. The thickness of film was controlled by the total charge during polymerisation. FTIR spectra were obtained using a Bio-RAD FTS-60 FTIR spectrometer with nitrogen purging (FIG. 4).
(d) Evaluation of Poly(PPy-co-PAA) as DNA Sensor
Covalent Immobilisation of ODN Probes onto the Copolymer Film To covalently attach the ODN probe to the polymer-coated electrode, 40 μl of phosphate buffer (pH 5.2) containing 13 μmol NaCl, 20 nmol ODN probe and 400 nmol EDC was added and kept at 28° C. for 1 h. The modified electrode was thoroughly washed using PBS solution to remove any free ODN probe.
Hybridization of Sample ODNs Hybridization of sample (complementary) ODNs with the ODN probe on the sensor was carried out by incubating the sensor film in PBS solution for 1 h at 42° C. After hybridization, the film was washed three times using PBS solution for 5 min to remove any non-hybridized ODNs. In order to investigate the sensitivity of the sensor, various concentrations of complementary ODNs were used. FIG. 5 presents AC impedance results.

Figure 6:
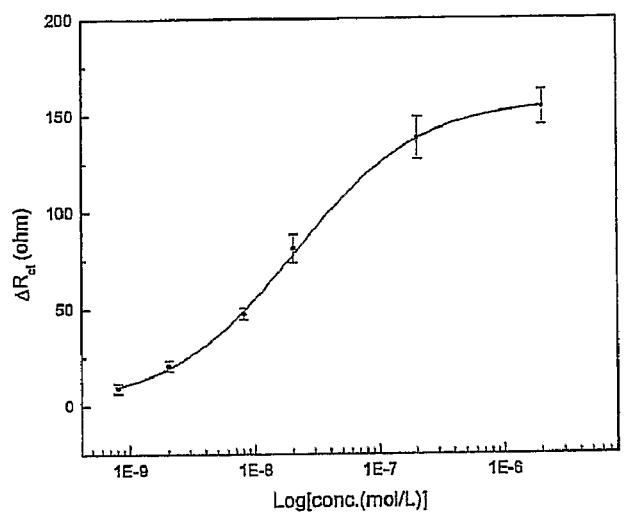
FIG. 6 Calibration curve corresponding to the changes in the charge transfer resistances of the electrodes modified with poly(Py-co-PAA) upon interaction with different concentrations of the complementary ODN.

The sensory properties of the obtained film were evaluated by means of AC impedance spectroscopy. FIG. 5 presents these results. The curves on FIG. 5 were fitted with the equivalent circuit (see FIG. 5) and the obtained values of charge transfer resistance ($R_{ct}$) were taken as an index of the sensor response. The procedure was repeated for a number of ODN target concentration and the obtained calibration graph is shown in FIG. 6.

Figure 7:
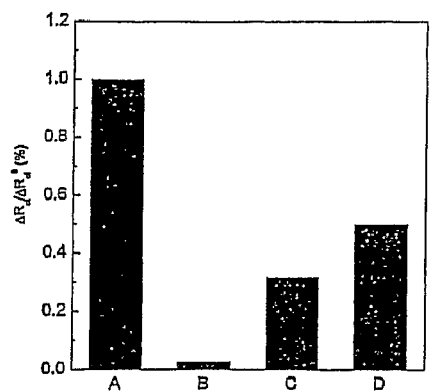
FIG. 7 Normalised changes in the charge transfer resistances of the sensor based on poly(Py-co-PAA) film after hybridization with different sequences of ODN (20.2 nM) (A) complementary ODN; (B) non-complementary ODN; (C) two-points mismatch ODN; (D) one-point mismatch ODN. $\Delta R_{ct}^0$ is the change in the charge transfer resistance of the sensor hybridized with complementary ODN.

Selectivity of the poly(PPy-co-PAA) sensor film towards one- and two-point mismatches was also examined (FIG. 7).

Figure 8:
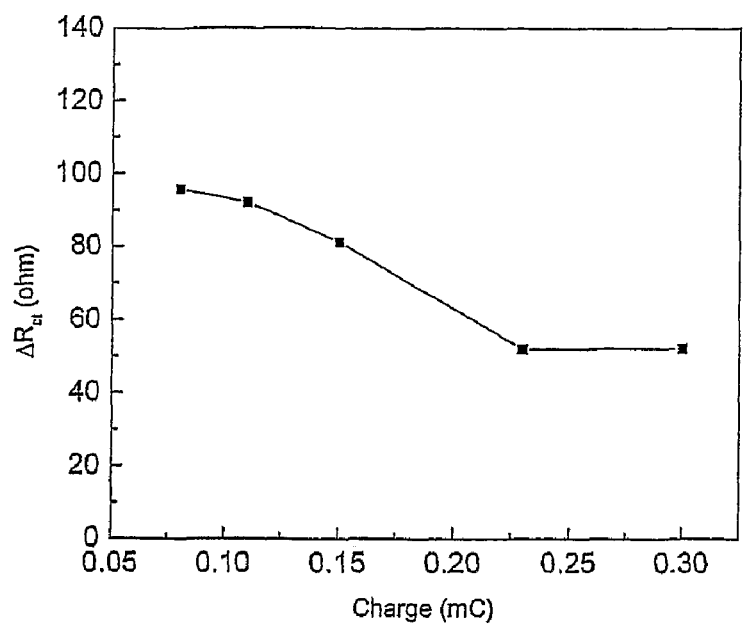
FIG. 8 Dependence of the change in $R_{ct}$ on the film thickness for poly(Py-co-PAA) films.

We have also investigated the effect of poly(Py-co-PAA) film thicknesses on the changes in the charge transfer resistances after the hybridization with 20.2 nmol complementary ODN. The thickness of the film was controlled by the amount of the charge passed for the film synthesis (see FIG. 8).
(a) Synthesis The synthetic route for a functionalised monomer of the general formula IV, 5-(1H-pyrrol-3-yl) 2,4-pentadienoic acid synthesis, is outlined in the Scheme II.

EXAMPLE 2

Synthesis of a Functionalised Monomer of the General Formula V (5-(1H-pyrrol-3-yl) 2,4-pentadienal 17 and its (co)polymer and the Evaluation as a DNA Sensor Scheme II Synthetic route to 5-(1H-pyrrol-3-yl) 2,4-pentadienal (PPDA) 17

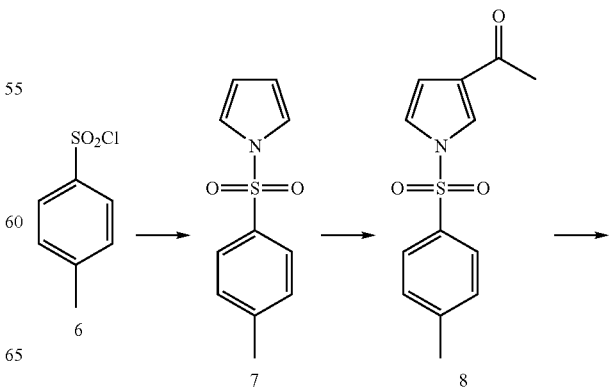

-continued

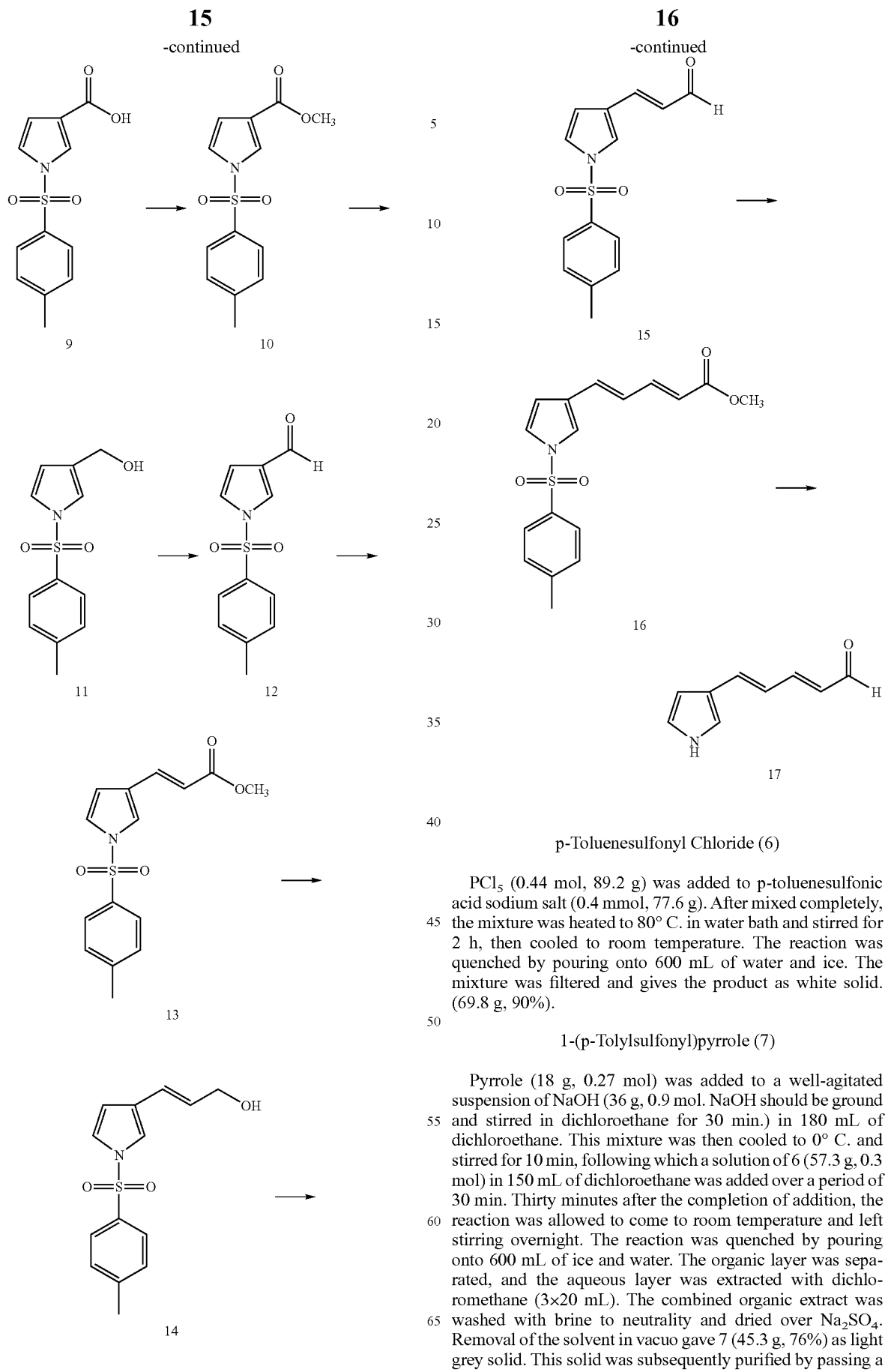

p-Toluenesulfonyl Chloride (6)

PCl$_5$ (0.44 mol, 89.2 g) was added to p-toluenesulfonic acid sodium salt (0.4 mmol, 77.6 g). After mixed completely, the mixture was heated to 80° C. in water bath and stirred for 2 h, then cooled to room temperature. The reaction was quenched by pouring onto 600 mL of water and ice. The mixture was filtered and gives the product as white solid. (69.8 g, 90%).

1-(p-Tolylsulfonyl)pyrrole (7)

Pyrrole (18 g, 0.27 mol) was added to a well-agitated suspension of NaOH (36 g, 0.9 mol. NaOH should be ground and stirred in dichloroethane for 30 min.) in 180 mL of dichloroethane. This mixture was then cooled to 0° C. and stirred for 10 min, following which a solution of 6 (57.3 g, 0.3 mol) in 150 mL of dichloroethane was added over a period of 30 min. Thirty minutes after the completion of addition, the reaction was allowed to come to room temperature and left stirring overnight. The reaction was quenched by pouring onto 600 mL of ice and water. The organic layer was separated, and the aqueous layer was extracted with dichloromethane (3×20 mL). The combined organic extract was washed with brine to neutrality and dried over Na$_2$SO$_4$. Removal of the solvent in vacuo gave 7 (45.3 g, 76%) as light grey solid. This solid was subsequently purified by passing a concentrated solution in dichloromethane through an alumina column (35.4 g). $^1$H NMR (CDCl$_3$, δ/ppm), 7.75 (m, 2H), 7.29 (m, 2H), 7.15 (t, 2H), 6.28 (t, 2H).

3-Acetyl-1-(p-Tolylsulfonyl)pyrrole (8)

To a suspension of AlCl$_3$ (64 g, 0.48 mol) in 200 mL of 1,2-dichloroethane was added at 25° C. acetic anhydride (16 g, 0.16 mol), and the mixture was stirred at 25° C. for 15 min. A solution of 7 (0.16 mol, 35.4 g,) in 200 mL of 1,2-dichloroethane was added, and the mixture was stirred at 25° C. for 2 h. The reaction was quenched with ice and water (500 mL) and the product extracted with dichloromethane. The organic layer was washed with water, dried over Na$_2$SO$_4$ and concentrated to give 8 as a brown solid (31.7 g, 85%). The crude product was purified by flash chromatography (silica gel, hexane:ethyl acetate=2:1). $^1$H NMR (CDCl$_3$, δ/ppm), 7.81 (d, 2H), 7.73 (t, 1H), 7.35 (d, 2H), 7.14 (m, 1H), 6.68 (m, 1H), 3.73 (s, 3H), 2.42 (s, 3H)

1-(p-Tolylsulfonyl)pyrrole-3-carboxylic acid (9)

500 mL of sodium hydroxide aqueous solution (12%) was cooled to 0° C. Bromine (60 g, 375.5 mmol) was added carefully, followed by the addition of 100 mL dioxane. The resulting hypobromite solution was kept at 0° C. before use.

To a solution of 8 (25 g, 0.11 mol) in dioxane (1 L) and water (250 mL) at 0° C. was added a steady stream of a cold hypobromite solution while stirring. After 2 h, acetone (250 mL) was added and the resulting solution was acidified with concentrated HCl to pH 1, and the mixture was extracted with dichloromethane for three times. The combined organic extracts were washed with saturated aqueous sodium bicarbonate, water and brine, dried over sodium sulphate, filtered and evaporated to give brown solid 9 (24.5, 95%) which was purified by flash chromatography (silica gel, hexane:ethyl acetate=1:1). $^1$H NMR (CDCl$_3$, δ/ppm), 7.78-7.83 (m, 3H), 7.34 (d, 2H), 7.13 (m, 1H), 6.68 (m, 1H), 2.42 (s, 3H); $^{13}$C NMR (CDCl$_3$, δ/ppm), 167.1, 145.0, 134.1, 129.3, 126.3, 125.2, 120.3, 118.7, 112.5, 20.7.

Methyl 1-(p-Tolylsulfonyl)pyrrole-3-carboxylate (10)

Sulfuric acid (10 mL) was added to the solution of 9 (20, 0.085 mol) in 200 mL of methanol and the whole was refluxed overnight. Water (200 mL) was then added to the solution and the resulting mixture was extracted with dichloromethane for three times. The combined organic extracts were washed with saturated aqueous sodium bicarbonate, water and brine, dried over sodium sulphate, filtered and evaporated to give brown solid which was purified by silica gel chromatography (hexane:ethyl acetate=3:1) to give 10 as white crystal (15.6 g, 75%). $^1$H NMR (CDCl$_3$, δ/ppm), 7.79 (d, 2H), 7.75 (t, 1H), 7.33 (d, 2H), 7.11 (m, 1H), 6.65 (m, 1H), 3.80 (s, 3H), 2.42 (s, 3H)

1-(p-Tolylsulfonyl)-3-pyrrolylmethanol (11)

To a solution of 10 (15.6 g, 0.063 mol) in 250 mL anhydrous THF was added LiBH$_4$ (1.8 g, 0.08 mol) at 60° C. water bath for 24 h. The reaction was quenched by the addition of 1 M H$_2$SO$_4$ solution. The resulting solution was extracted with dichloromethane. The extracts were washed with saturated aqueous sodium bicarbonate, water and brine, dried over sodium sulphate, filtered and evaporated under vacuum to give light yellow solid which subjected to flash chromatography (silica gel, hexane:ethyl acetate=2:1) to afford 11 as a white solid (14.3 g, 90%). $^1$H NMR (CDCl$_3$, δ/ppm), 7.74 (m, 2H), 7.29 (d, 2H), 7.12-7.09 (m, 2H), 6.29 (m, 1H), 4.46 (s, 2H), 2.39 (s, 3H), 1.86 (b, 1H).

1-(p-Tolylsulfonyl)pyrrole-3-carboxaldehyde (12)

Manganese dioxide (100 g) was added to the solution of 11 (14.3 g, 0.057 mol) in 250 mL chloroform and the mixture was refluxed for 12 h. The mixture was then filtered and the filtrate was concentrated under vacuum to afford a yellow oil which subjected to flash chromatography (silica gel, hexane: ethyl acetate=2:1) to afford 12 as a white solid (7.2 g, 51%). $^1$H NMR (CDCl$_3$, δ/ppm), 9.97 (s, 1H), 7.81 (m, 2H), 7.63 (m, 1H), 7.34 (d, 2H), 7.16 (m, 1H), 6.40 (t, 1H), 2.42 (s, 3H).

3-(1-(p-Tolylsulfonyl)pyrrol-3-yl)-acrylic acid methyl ester (13)

(Triphenylphosphoranylidene) methyl acetate (43 mmol, 15 g, 1.5 equiv) was added to a solution of 12 (7.2 g, 0.029 mmol) in anhydrous THF (250 mL). The reaction mixture was stirred at 50° C. for 4 h and concentrated in vacuo to give a light yellow solid, which upon purification by column chromatography on silica gel (hexane/ethyl acetate=2:1) gave the product 13 (8.4 g, 95%). $^1$H NMR (CDCl$_3$, δ/ppm), 7.78 (m, 2H), 7.51 (d, 1H), 7.32-7.29 (m, 3H), 7.34 (d, 2H), 7.14 (m, 1H), 6.48 (m, 1H), 6.15 (d, 1H), 3.76 (s, 3H), 2.41 (s, 3H).

3-(1-(p-Tolylsulfonyl)pyrrol-3-yl)-2-Propenol 14

To a solution of 13 (3 g, 10 mmol) in 150 mL anhydrous THF was added LiBH$_4$ (0.27 g, 12 mmol) under nitrogen and the mixture was stirred at room temperature for 24 h. The reaction was quenched by the addition of 1 M H$_2$SO$_4$ solution. The resulting solution was extracted with dichloromethane. The extracts were washed with saturated aqueous sodium bicarbonate, water and brine, dried over sodium sulphate, filtered and evaporated under vacuum to give light yellow solid which subjected to flash chromatography (silica gel, hexane:ethyl acetate=2:1) to afford 14.

3-(1-(p-Tolylsulfonyl)pyrrol-3-yl)-2-Propenal (15)

Method a: To a suspension of Dess-Martin periodinane (85.0 mg) in 5 ml of CH$_2$Cl$_2$, was added 14 (2 g) in 100 ml CH$_2$Cl$_2$ at room temperature. After stirring for 2 h, the reaction mixture was treated with aqueous Na$_2$S$_2$O$_3$ and aqueous NaHCO$_3$. The organic layer was washed with brine, dried over Na$_2$SO$_4$, filtered, and the solvent was removed under reduced pressure to give crude products. The crude products were subjected to flash chromatography (silica gel, hexane: ethyl acetate=2:1) to afford 15.

Method b: Manganese dioxide (10 g) was added to the solution of 14 (2 g) in 100 mL chloroform and the mixture was refluxed for 12 h. The mixture was then filtered and the filtrate was concentrated under vacuum to afford a yellow oil which subjected to flash chromatography (silica gel, hexane: ethyl acetate=2:1) to afford 15 as a white solid. (0.5 g, 50%). $^1$H NMR (CDCl$_3$, δ/ppm), 9.60 (d, 1H), 7.80 (m, 2H), 7.43 (t, 1H), 7.34-7.27 (m, 3H), 7.19 (m, 1H), 6.51 (m, 1H), 6.45 (m, 1H), 2.42 (s, 3H).

5-(1-(p-Tolylsulfonyl)pyrrol-3-yl)-2,4-Pentadienoic acid methyl ester (16)

(Triphenylphosphoranylidene) methyl acetate (3 mmol, 1.05 g, 1.5 equiv) was added to 15 (0.502 g,) in anhydrous THF (30 mL). The reaction mixture was stirred at 50° C. for 4 h and concentrated in vacuo to give crude products of 16, which are purified by column chromatography on silica gel (hexane/ethyl acetate=3:1) to afford 16 as light yellow solid (0.35 g). $^1$H NMR (CDCl$_3$, δ/ppm), 7.77 (m, 2H), 7.39-7.29 (m, 3H), 7.23 (m, 1H), 7.13 (m, 1H), 6.73 (d, 1H), 6.60 (m, 1H), 6.47 (m, 1H), 5.92 (d, 1H), 3.73 (s, 3H), 2.42 (s, 3H).

5-(1H-pyrrol-3-yl) 2,4-pentadienoic acid (17)
(PPDA; General formula V)

16 (1 g, 3 mmol) was placed in 30 mL of 1:1 (v:v) mixture of MeOH and 2 M aqueous NaOH and refluxed for 5 h, after which time the reaction mixture was allowed to cool and methanol was removed in vacuum. The aqueous solution was acidified with 5 M HCl to pH 3 and the precipitate was collected and dried in vacuum oven to give 17 as light green powder. (0.4 g, 81%). IR, 3424, 3500-2500, 1691, 1597, 1531, 1499, 1344, 1265, 1149, 1075, 989; $^1$H NMR (DMSO-d$_6$, δ/ppm), 11.92 (s, 1H), 11.02 (s, 1H), 7.31 (m, 1H), 7.03 (m, 1H), 6.94 (d, 1H), 6.78 (m, 1H), 6.62 (m, 1H), 6.34 (m, 1H), 5.76 (d, 1H), 5.92 (d, 1H), 3.73 (s, 3H), 2.42 (s, 3H). $^{13}$C NMR δ/ppm, 168.95, 146.98, 136.76, 122.26, 121.99, 121.43, 120.86, 118.25, 106.35.

(b) Chemical Polymerisation of 5-(1H-pyrrol-3-yl) 2,4-pentadienoic acid (PPDA)

Figure 9:
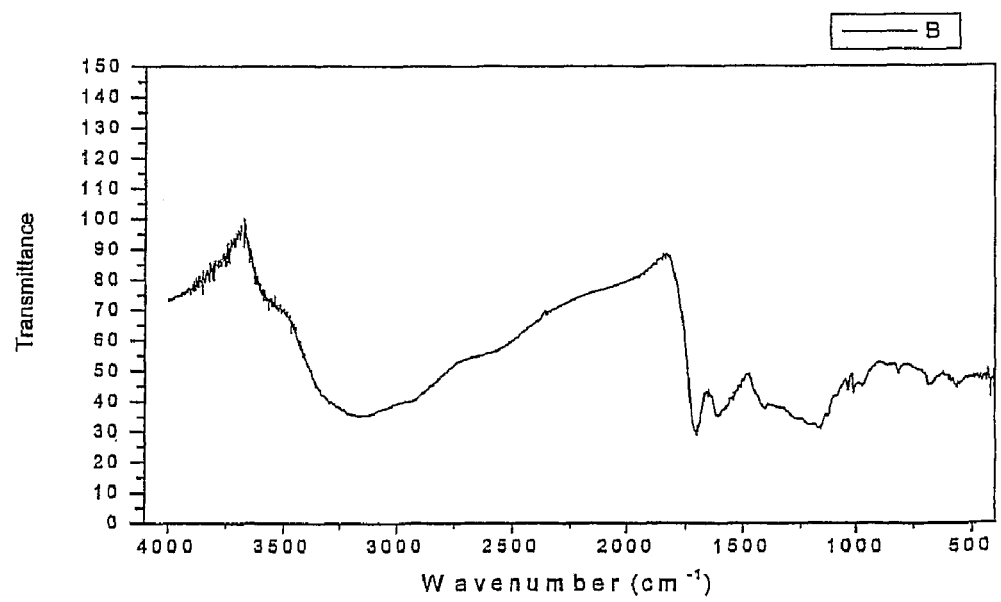
FIG. 9 FTIR spectra of poly(PPDA).

0.20 g FeCl$_3$ was added to PPDA solution (0.10 g) and the mixture was stirred for 5 h. The precipitate was collected, washed with acetone and water and dried in vacuum oven. FIG. 9 shows the obtained FTIR spectra.

(c) Electrocopolymerisation of Poly(PPy-co-PPDA)

Figure 10:
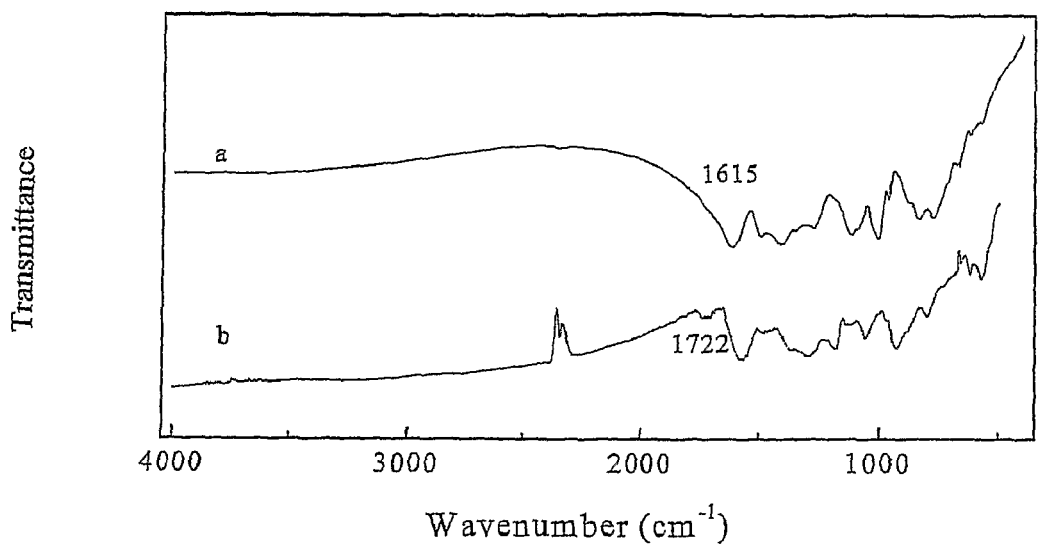
FIG. 10 FTIR spectra of polypyrrole (a) and poly(Py-co-PPDA).

The electrochemical synthesis of poly(Py-co-PPDA) films was carried out by using CH Instrument electrochemical workstation (Model 440, CH Instruments, USA) at a fixed potential of 1.0 V (Ag/AgCl,). A three-electrode cell with a volume of 3.0 mL, comprising a glassy carbon working electrode (BAS, 3.0 mm in diameter), an Ag/AgCl (3M KCl) reference electrode and Pt wire counter electrode, was used. Prior to electropolymerisation, glassy carbon electrodes were polished with a 0.5 μm alumina slurry (Allied Tech Products, Inc, USA), then washed with acetone, ethanol and Milli-Q water. The polymerisation solution contains 0.5 M Py, 6.25 mM PPDA, and 0.2 M LiClO$_4$ in 2 mL acetonitrile or propylene carbonate. The thickness of film was controlled by the total charge during polymerisation. FTIR spectra were obtained using a Bio-RAD FTS-60 FTIR spectrometer with nitrogen purging (FIG. 10).

(d) Evaluation of poly(PPy-co-PPDA) as DNA Sensor
Covalent Immobilisation of ODN Probes onto the Copolymer Film To covalently attach the ODN probe to the polymer-coated electrode, 40 μl of phosphate buffer (pH 5.2) containing 13 μmol NaCl, 20 nmol ODN probe and 100 mmol EDC was added and kept at 28° C. for 1 h. Finally, the modified electrode was thoroughly washed using PBS solution to remove any free ODN probe.

Hybridization of Sample ODNs

Hybridization of sample (complementary) ODNs with the ODN probe on the sensor was carried out by incubating the sensor film in PBS solution for 1 h at 42° C. After hybridization, the film was washed three times using PBS solution for 5 min to remove any non-hybridized ODNs. In order to investigate the sensitivity of the sensor, various concentrations of complementary ODNs were used.

Figure 11:
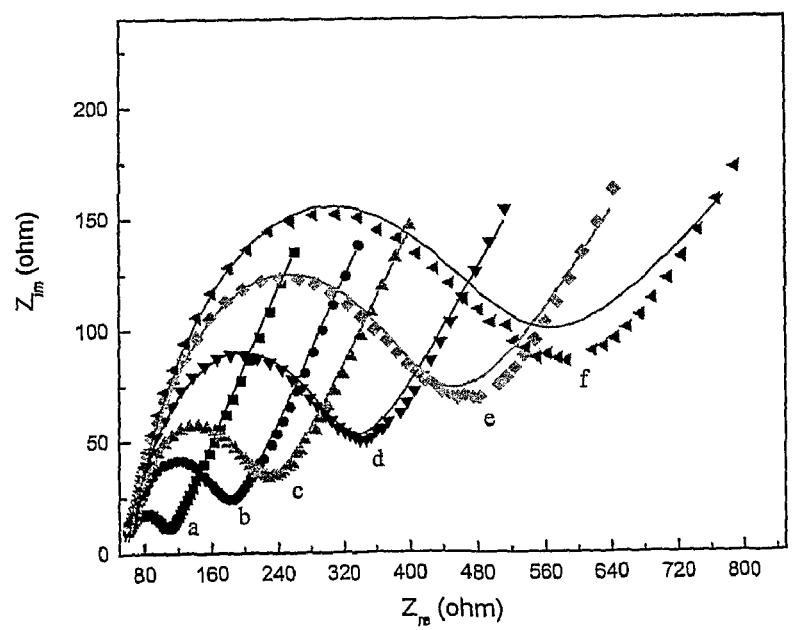
FIG. 11 Nyquist plots (-Zim vs Zre) for electrochemical impedance measurement based on electrodes coated with poly(Py-co-PPDA) in PBS solution (pH 7.4) containing 5.0 mM $Fe(CN)_6^{3-}/Fe(CN)_6^{4-}$ before immobilisation of the ODN probes a); after immobilisation of ODN probes (b); after hybridization with 2 nM (c), 20 nM (d), 200 nM (e) and 2 μM (f) complementary ODNs. In all cases, the experimental data are shown as symbols and the fitting data as solid lines.
Figure 12:
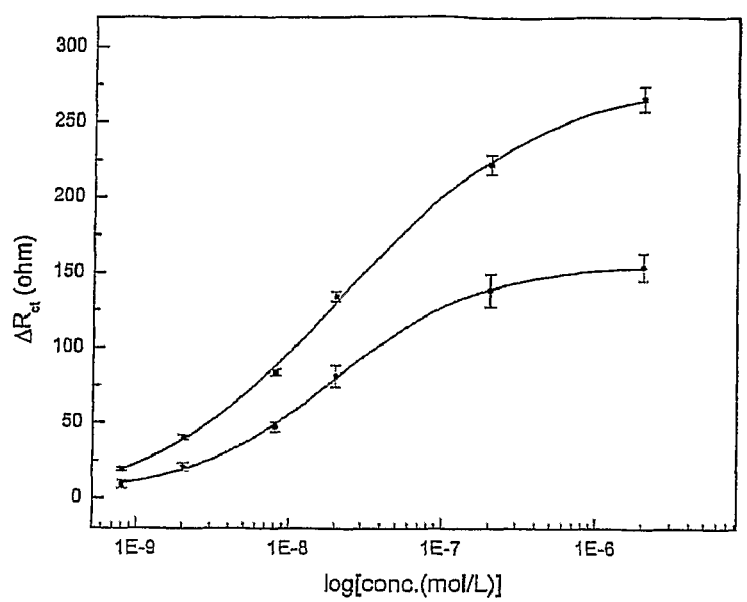
FIG. 12 Calibration curves corresponding to the changes in the charge transfer resistances of the electrodes modified with poly(Py-co-PPDA) (a) and poly(Py-co-PAA) (b) (included for comparison) upon interaction with different concentrations of the complementary ODN.

As above, the sensory properties of the obtained film were evaluated by means of AC impedance spectroscopy. The resulting AC impedance spectra are shown in FIG. 11 and the calibration graph, based on the $R_{ct}$ values obtained from fitting procedures, on FIG. 12. The calibration curve for poly(PPy-co-PAA), obtained in Example 1, is included into the FIG. 12 for comparison purposes.

Figure 13:
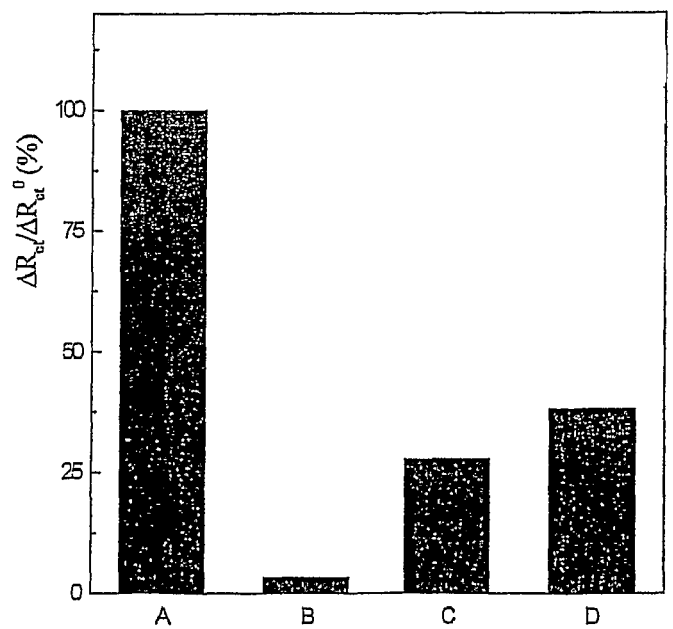
FIG. 13 Normalised changes in the charge transfer resistances of the sensor based on poly(Py-co-PPDA) film after hybridization with different sequences of ODN (20.2 nmol) (A) complementary ODN; (B) non-complementary ODN; (C) two-points mismatch ODN; (D) one-point mismatch ODN. $\Delta R_{ct}^0$ to is the change in the charge transfer resistance of the sensor hybridized with complementary ODN.

The selectivity of the poly(PPy-co-PPDA) sensor film toward discrimination of one- and two-point mismatches is shown in FIG. 13.

Figure 14:
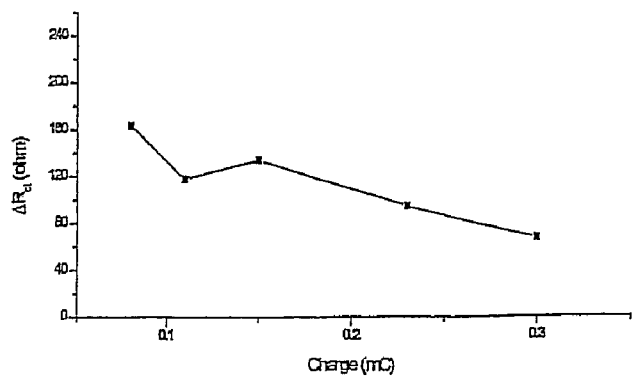
FIG. 14 Dependence of the change in $R_{ct}$ on the film thickness for poly(Py-co-PPDA) films.

The effect of poly(Py-co-PAA) film thicknesses on the changes in the $R_{ct}$ after the hybridization with 20.2 nmol complementary ODN is presented in FIG. 14.

(e) Summary of Results

Table 1 (below) shows that poly(Py-co-PPDA) film shows similar charge transfer resistance ($R_{ct}$) to poly(Py-co-PAA) film before immobilization of ODN probe. After immobilization of ODN probe, the changes in the charge transfer resistances are 118.9 ohm and 64.4 ohm for poly(Py-co-PAA) and poly(Py-co-PPDA), respectively.

After hybridization with 20.2 nM ODN target, poly(Py-co-PPDA) film shows better sensory property seen by the larger change in $R_{ct}$ then in the case of poly(PPA-co-PAA), 134.4 ohms vs. 81.2 ohms. This indicates that the probe-target complex immobilized on poly(Py-co-PPDA) film is more strongly perturbing the electronic structure of the polymer in the case of poly(Py-co-PPDA) and induces larger changes in the film electrochemical properties.

In addition, the longer length of the PPDA linker allows more efficient hybridization (less steric hindrances).

TABLE 1

Impedance parameters obtained by modelling of the AC impedance by Equivalent Circuit, for the poly(Py-co-PAA) and poly(Py-co-PPDA) copolymer films obtained after copolymerisation, after ODN probe immobilization, and after hybridization with complementary ODN sequences.

|  | $R_s$ (Ω) | CPE (μF) | $R_{ct}$ (Ω) |
|---|---|---|---|
| Poly(Py-co-PAA) coated electrode |  |  |  |
| Before immobilization (curve a) | 57.8 ± 0.4 | 5.04 ± 0.38 | 54.9 ± 0.8 |
| After immobilization (curve b) | 59.5 ± 0.4 | 4.89 ± 0.25 | 173.8 ± 2.7 |
| After hybridization with 20.2 nM ODN target (curve d) | 57.6 ± 0.4 | 4.21 ± 0.64 | 255.0 ± 13.3 |
| Poly(Py-co-PPDA) coated electrode |  |  |  |
| Before immobilization (curve a) | 54.4 ± 0.6 | 5.16 ± 0.75 | 51.0 ± 1.1 |
| After immobilization (curve b) | 58.4 ± 0.4 | 4.65 ± 0.39 | 115.4 ± 1.7 |
| After hybridization with 20.2 nM ODN target (curve d) | 58.9 ± 0.4 | 4.12 ± 0.23 | 249.8 ± 3.5 |

Thus the improved sensory properties of poly(Py-co-PPDA) can be explained in several ways:

a) Extended conjugation in the 5-(1H-pyrrol-3-yl) 2,4-pentadienoic acid (PPDA) side chain gave a polymer with better electronic properties (e.g. conductivity) due to the electron-donating characteristics of the side chain and therefore the polymer is more susceptible to the perturbation in its electronic structure;

b) Extended conjugation allowed the direct electronic communication between the main polymer backbone and the biorecognition probe (ODN);

c) The side chains with unsaturated bonds are stiffer then those with saturated carbon-carbon bonds, giving better orientation of the attached ODN probes to the approach by complementary target ODN and subsequent hybridization.

EXAMPLE 3

Synthesis of 3-Pyrrolylpentanoic Acids Copolymerisation and Evaluation as a DNA Sensor 3-pyrrolylpentanoic acid (PPA) provides a functionalised monomer having a 5 carbon saturated linker. The 5 carbon saturated linker is included herein as a contrast to linkers which are unsaturated organic linker.

(a) Synthesis of 3-Pyrrolylpentanoic Acid

Scheme III Synthetic route to 3-pyrrolylpentanoic acid 20

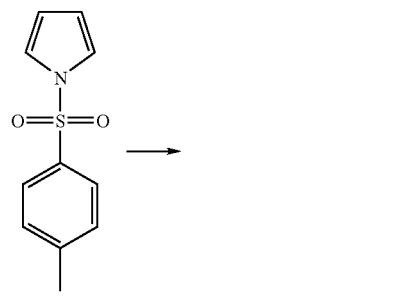

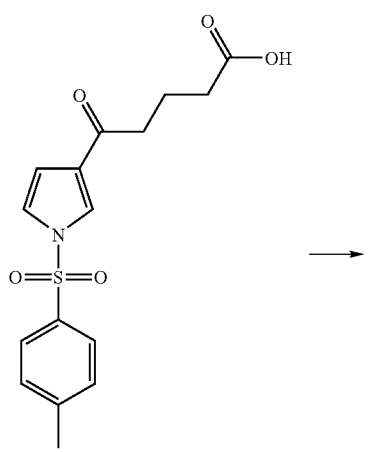

18

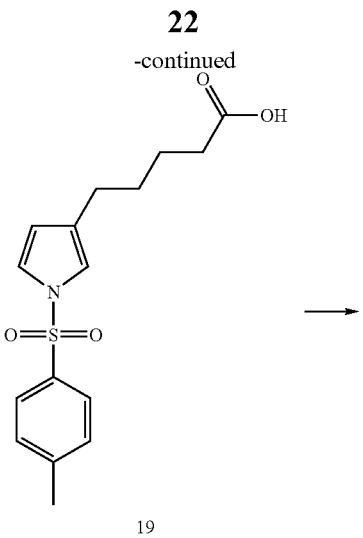

19

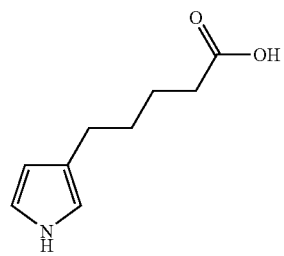

20

[(N-p-tolylsulfonyl)-3-pyrrolyl]-1'-oxypentanoic Acid (18)

To a suspension of AlCl₃ (13.30 g, 0.10 mol) in CH₂Cl₂ (250 mL) was added glutaric anhydride (5.7 g, 50 mmol). After stirring for 15 min a solution of 1-(p-Tolylsulfonyl) pyrrole (44.87 mmol) in CH₂Cl₂ (30 mL) was added slowly from a dropping funnel. The mixture was stirred for 12 h after which time the reaction was quenched with ice/water. The organic phase was separated, washed with fresh water, and dried over Na₂SO₄. Removal of the solvent under vacuum gave a dark oil 18. 1H NMR CDCl₃ δ/ppm: 7.92 m, 7.79 m, 7.66 m, 7.15 m, 6.70 m, 2.85 t, 2.46 t, 2.01 m.

[(N-p-tolylsulfonyl)-3-pyrrolyl]pentanoic Acid (19)

Amalgamated zinc (3.66 g 55.97 mmol) was added to a solution containing HgCl₂ (0.37 g, 1.36 mmol) in distilled water (5 mL) and 36% aqueous HCl (0.5 mL). After 10 min the amalgam was filtered and washed with fresh water. 18 (2.25 g, 7.00 mmol) was added to a flask containing the amalgamated zinc in a solution of toluene (25 mL), distilled water (5.5 mL), and 36% aqueous HCl (3 mL). This mixture was refluxed with vigorous stirring for 24 h and cooled. The toluene phase was separated, washed once with brine, and dried over Na₂SO₄. Removal of toluene under vacuum gave [(N-phenylsulfonyl)-3-pyrrolyl]pentanoic acid 19 (1.90 g, 6.18 mmol).

3-Pyrrolylpentanoic Acid (20)

19 (5.86 mmol) was placed in 30 mL of 1:1 (v:v) mixture of MeOH and 8 M aqueous NaOH and refluxed for 5 h. The reaction mixture was allowed to cool and methanol was removed in vacuo, The aqueous solution was acidified with 5 M HCl to pH 3 and thoroughly extracted with ethyl acetate. After removing most of solvent, the mixture was passed a silica column to give 20. (Hexane:Ethyl acetate=2:1). $^{1}$H NMR CDCl$_3$ δ/ppm: 10.49 bs, 6.72 m, 6.62 m, 5.99 m, 2.51 t, 2.35 t, 1.64 m.

(b) Electrocopolymerisation of Poly(PPy-co-PPA) in Acetonitrile and Propylene Carbonate, and Evaluation of the Sensors' Properties A three-electrode cell with a volume of 3 mL, comprising a glassy carbon working electrode (3 mm diameter), an Ag/AgCl (3M KCl) reference electrode and Pt wire counter electrode, was used. Prior to electropolymerisation, the working electrode was polished mechanically (6, 3 and 1 μm grid) and then with 0.5 μm alumina slurry and thoroughly washed with Milli-Q water, ethanol and acetone.

Figure 15:
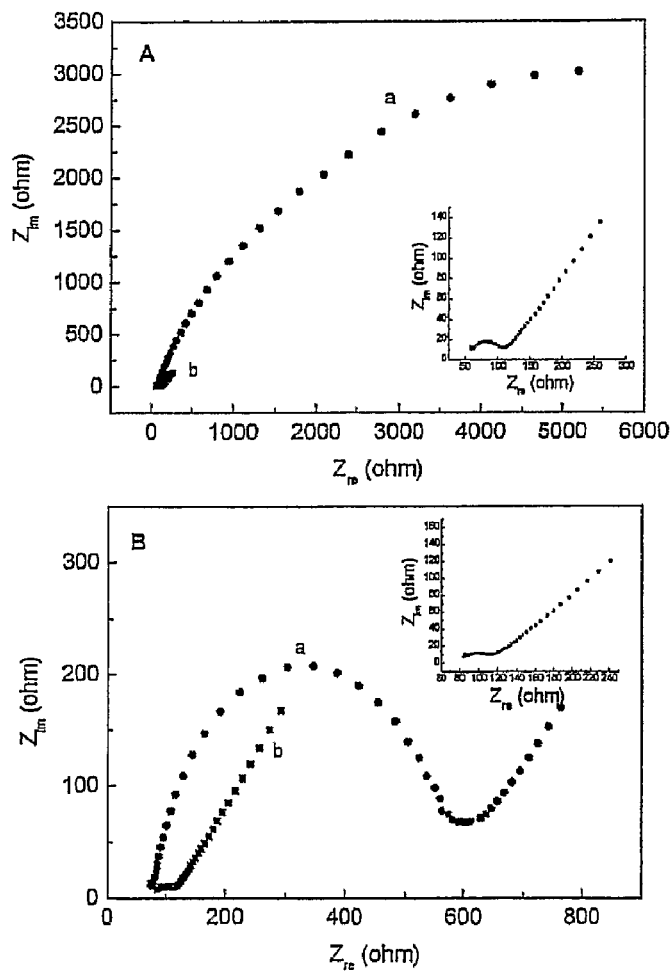
FIG. 15 Effect of solvents on properties of copolymer films. (A) films prepared in acetonitrile. (B) films prepared in propylene carbonate. a: poly(Py-co-PPA) film; b: poly(Py-co-PPDA) film. The films were prepared by passing a charge of 0.15 mC.

The copolymer film was synthesized in either actetonitrile or propylene carbonate from 0.5 M pyrrole, 6.25 mM PPA, 0.2 M LiClO$_4$ by a potentiostatic method at a fixed potential of 1.0 V. The electrolyte solution was deaerated by purging with nitrogen before use. The electropolymerisation was stopped when the total charge supplied by the electrode reached the desired value. FIG. 15 compares the AC impedance spectra of Poly(Py-co-PPA) and poly(Py-co-PPDA) films obtained in acetonitrile and propylene carbonate solvents.

Figure 16:
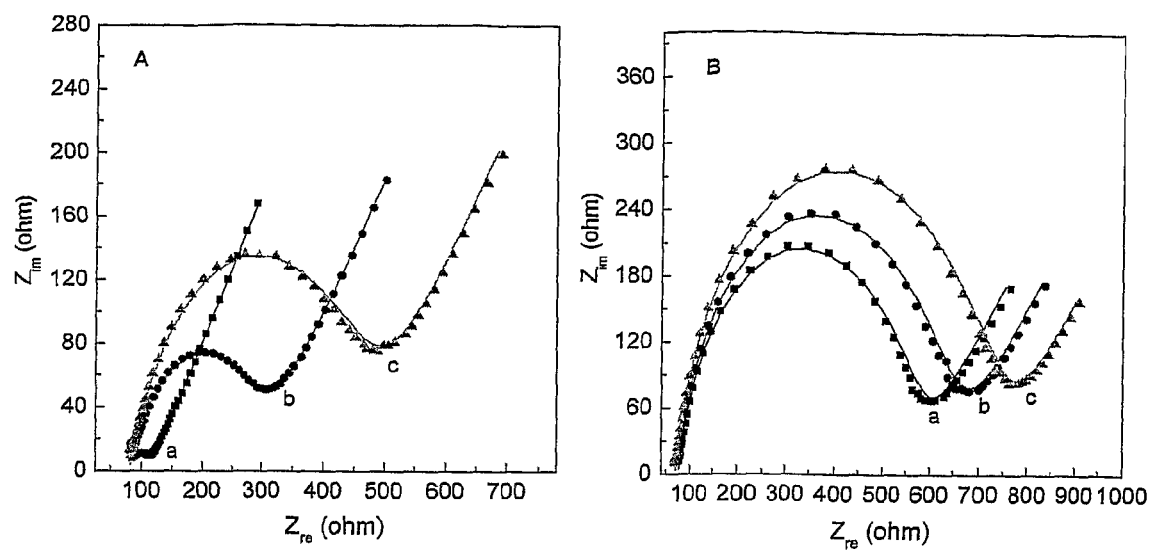
FIG. 16 (A) Sensor response based on poly(Py-co-PPDA) film prepared in propylene carbonate. (B) Sensor response based on poly(Py-co-PPA) film prepared in propylene carbonate (PAA, 3-Pyrrolylpentanoic Acid). a: before immobilisation of ODN probe; b: after immobilisation of ODN probe; c after incubation with 20.2 nM ODN target solution.

FIG. 16 compares the AC impedance responses of the poly(Py-co-PPDA) and poly(Py-co-PPA) films before and after covalent attachment of ODN probes, and after exposure of the sensor film to the complementary ODN sequences. The obtained charge transfer resistance change of the sensor film was 173.1 ohm for poly(Py-co-PPDA) film and 93.9 ohm for poly(Py-co-PPA) film.

(c) Summary of Results

To discriminate between the effects of having an unsaturated organic linker and the linker length we compared the responses of the two copolymer films, containing either the functionalised monomer with saturated linker or the functionalised monomer with unsaturated linker of the same length.

Comparing the AC impedance spectra of the poly(Py-co-PPA) (B) and poly(Py-co-PPDA) (of Example 2) (A) films before the attachment of the probe, one can see that these films have dramatically different properties. The film with PPDA has much lower $R_{ct}$ (35.5 ohms vs. 494.2 ohms). The changes in the AC impedance spectra of those two films after the probe immobilization and after hybridization, show that the poly(Py-co-PPDA) is much more sensitive to perturbations caused by the recognition event. The change in $R_{ct}$ upon the hybridization for poly(Py-co-PPDA) is 173.1 ohms and for poly(Py-co-PPA) film 93.9 ohms. The stronger change in $R_{ct}$ (taken as the index of the sensor response) implies the better sensor properties. The significantly improved sensor properties for poly(Py-co-PPDA) are due to the unsaturated side chain that connects probe to the polymer backbone and provide effective electronic communication between the two.

TABLE 2

Simulated Values of the Equivalent Circuit Elements for the Polymer Film Prepared in PC Solvent after ODN Probe Immobilization, and after Hybridization

|  | $R_s$ (Ω) | CPE (μF) | $R_{ct}$ (Ω) |
|---|---|---|---|
| Poly(Py-co-PPA) coated electrode |  |  |  |
| Before immobilization (curve a) | 76.4 ± 0.5 | 1.73 ± 0.08 | 494.2 ± 6.3 |
| After immobilization (curve b) | 74.5 ± 0.4 | 1.63 ± 0.07 | 561.7 ± 7.0 |
| After hybridization with 20.2 nM ODN target (curve d) | 74.3 ± 0.4 | 1.47 ± 0.07 | 655.6 ± 8.2 |
| Poly(Py-co-PPDA) coated electrode |  |  |  |
| Before immobilization (curve a) | 78.7 ± 0.5 | 11.8 ± 1.1 | 35.5 ± 0.8 |
| After immobilization (curve b) | 81.5 ± 0.4 | 8.38 ± 0.4 | 219.3 ± 2.1 |
| After hybridization with 20.2 nM ODN target (curve d) | 79.9 ± 0.6 | 5.62 ± 0.5 | 392.4 ± 8.9 |

EXAMPLE 4

Synthesis of functionalised monomer of the general formula (VIII) 3-((2':2",5":2'''-terthiophene)-3"-yl) acrylic acid and evaluation

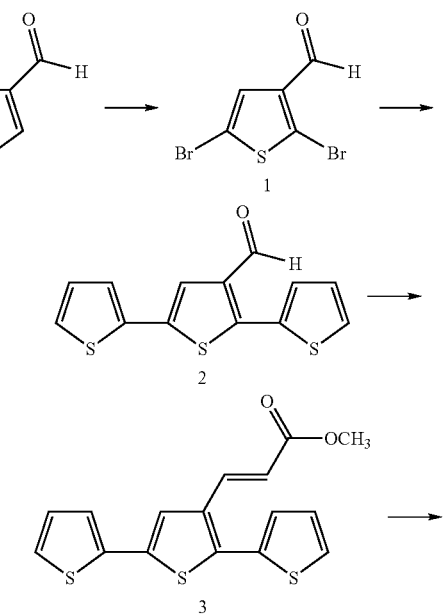

Scheme IV Synthesis of 3-((2':2", 5":2'''-terthiophene)-3"-yl) acrylic acid

2,5-Dibromo-3-formylthiophene (1)

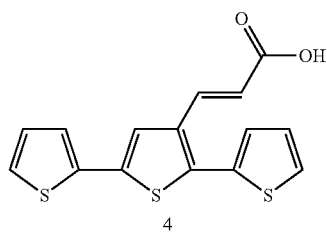

4

Thiophene-3-carboxaldehyde (2.54 g, 22.8 mmol) was mixed with 48% aqueous hydrobromic acid (6.8 mL), and ether (6 mL), then cooled at 0° C. A mixture of bromine (7.36 g, 46.0 mmol) and 48% aqueous hydrobromic acid (6.8 mL) was added dropwise under vigorous stir. The reaction mixture was then heated at 50° C. and reacted for 4 h. After reaction, the mixture was diluted with water (100 mL) and extracted with ether (3×50 mL). The organic layers were combined, washed with 10% sodium thiosulfate solution (2×15 mL) and water (30 mL), and dried ($Na_2SO_4$). The solvent was removed under reduced pressure to give dark crude product. The crude product was purified by column chromatography on silica gel (hexane/ethyl acetate=5:1). (4.32 g, 70%). $^1$H NMR (400 MHz, $CDCl_3$, δ/ppm) 9.80 (s, 1H, CHO), 7.34 (s, 1H);

3'-Formyl-2:2',5':2"-terthiophene (2)

Figure 17:
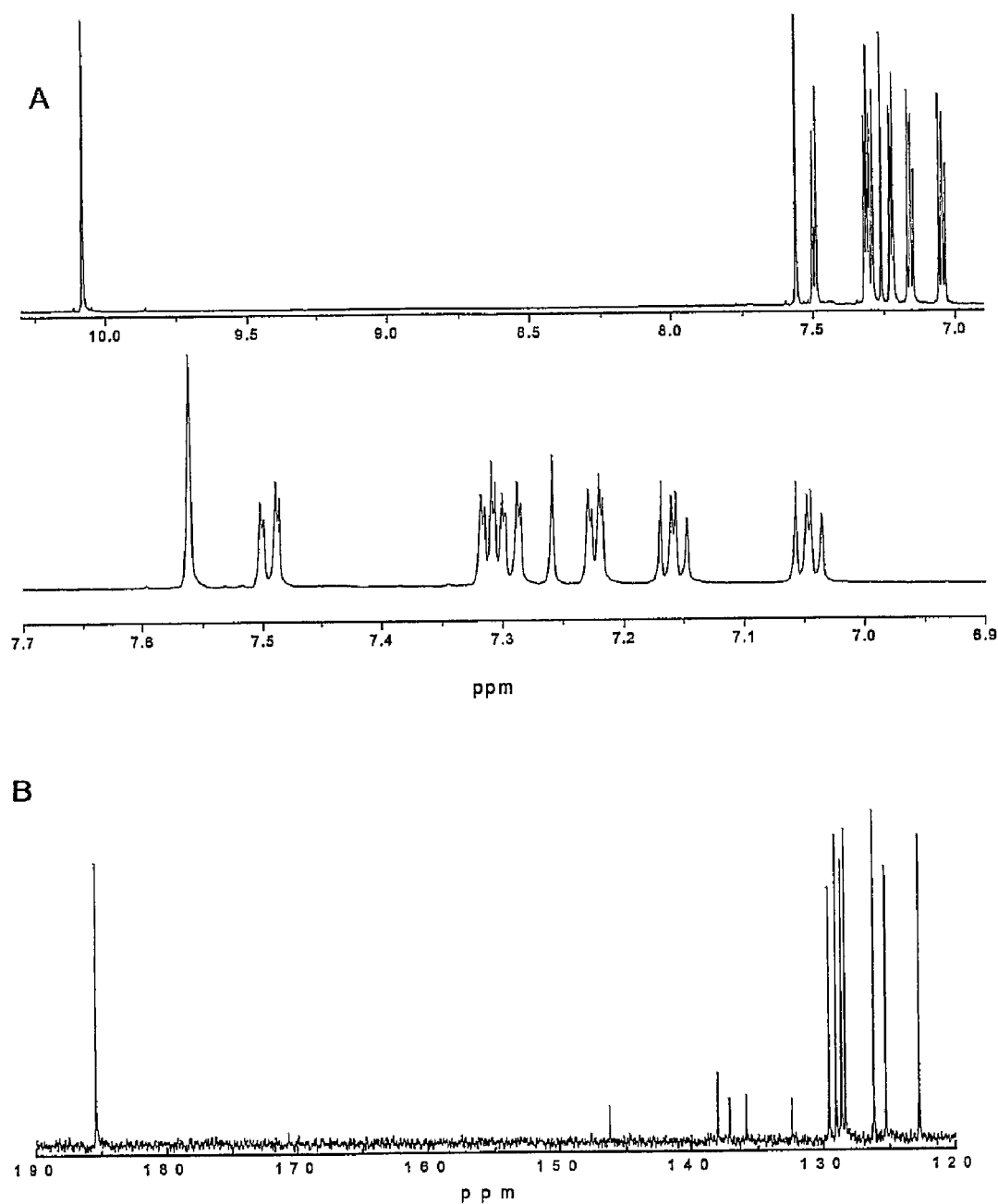
FIG. 17 (A) $^1$H NMR; and (B) $^{13}$C NMR spectra of 3'-formyl-2:2',5':2''-terthiophene.

2,5-dibromo-3-formylthiophene (1) (5.0 g, 18.5 mmol) and tetrakis (triphenyl phosphine) palladium [$Pd(PPh_3)_4$] (1.27 g, 1.1 mmol, 6 mmol %) was dissolved in 150 mL of 1,2-dimethoxyethane. 2-Thiophene boronic acid (5.42 g, 42.3 mmol) and a solution of 1 M $Na_2CO_3$ (110 mL) were added. The reaction mixture was heated under reflux for 5 h. Then another portion of 2-thiophene boronic acid (1.09 g, 8.5 mmol) was added and refluxed for overnight. The reaction mixture was concentrated under pressure and 150 mL of dichloromethane (150 mL) was added. The organic residue was washed with water (2×50 mL), dried ($Na_2SO4$). Removing the solvent in vacuum gives a brown liquid. This crude material was dissolved in $CH_2Cl_2$/hexane (1:1) and passed through a pad of silica to remove baseline material and the palladium catalyst. Further purification was carried out by column chromatography (hexane/ethyl acetate=6:1), followed by recrystallization from ether to give the compound (2) as a bright yellow solid (3.68 g, 72%): $^1$H NMR (400 MHz, $CDCl_3$, δ/ppm) 10.08 (s, 1H, CHO), 7.56 (s, 1H, H 4'), 7.50 (dd, 1H, H 5), 7.32 (dd, 1H, H 3), 7.30 (dd, 1H, H 5"), 7.23 (dd, 1H, H 3"), 7.16 (dd, 1H, H 4), 7.05 (dd, 1H, H 4"); $^{13}$C NMR (400 MHz, $CDCl_3$, δ/ppm) 185.5, 146.3, 138.1, 137.2, 135.9, 132.5, 129.6, 129.0, 128.7, 128.4, 126.2, 125.3, 122.8; (see, FIG. 17)

3-((2':2",5":2'''-terthiophene)-3"-yl)acrylic acid methyl ester (3)

Figure 18:
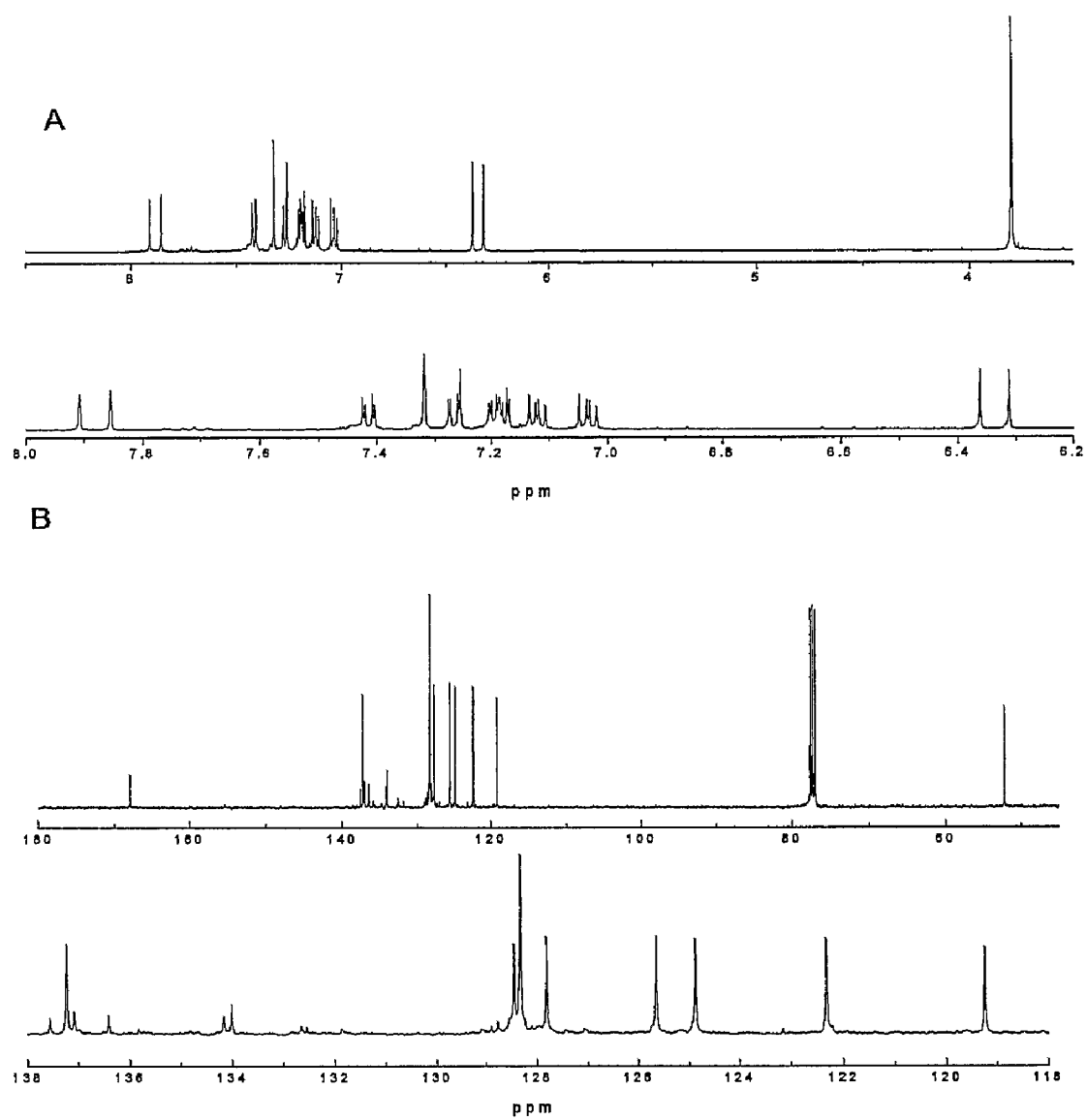
FIG. 18 (A) $^1$H NMR; and (B) $^{13}$C NMR spectra of 3-((2':2'',5'':2'''-terthiophene)-3''-yl)acrylic acid methyl ester.

(Triphenylphosphoranylidene) methyl acetate (7.6 mmol, 4 g, 1.5 equiv) was added to a solution of (2) (2.1 g, 7.6 mmol) in anhydrous THF (250 mL). The reaction mixture was stirred at 50° C. for 6 h and concentrated in vacuum to give a bright yellow solid, which upon purification by column chromatography on silica gel (hexane/ethyl acetate=5:1) gave the product (3) (2.1 g, 83%) $^1$H NMR ($CDCl_3$, δ/ppm), 7.90 (d, 1H, CH=CHCOOCH_3), 7.42 (dd, 1H, H 5'), 7.32 (s, 1H, H 4"), 7.27 (dd, 1H, H 3'), 7.20 (dd, 1H, H 5'''), 7.18 (dd, 1H, H 3'''), 7.14 (dd, 1H, H 4'), 7.04 (dd, 1H, H 4'''), 6.36 (d, 1H, CH=CHCOOCH_3); 3.79 (s, 3H); $^{13}$C NMR (400 MHz, $CDCl_3$, δ/ppm) 167.92, 137.57, 137.25, 137.09, 136.43, 134.18, 134.02, 128.78, 128.46, 128.34, 127.82, 125.66, 124.88, 122.34; 119.26, 52.07. (see, FIG. 18).

3-((2':2",5":2'''-terthiophene)-3"-yl)acrylic acid (4)

Figure 19:
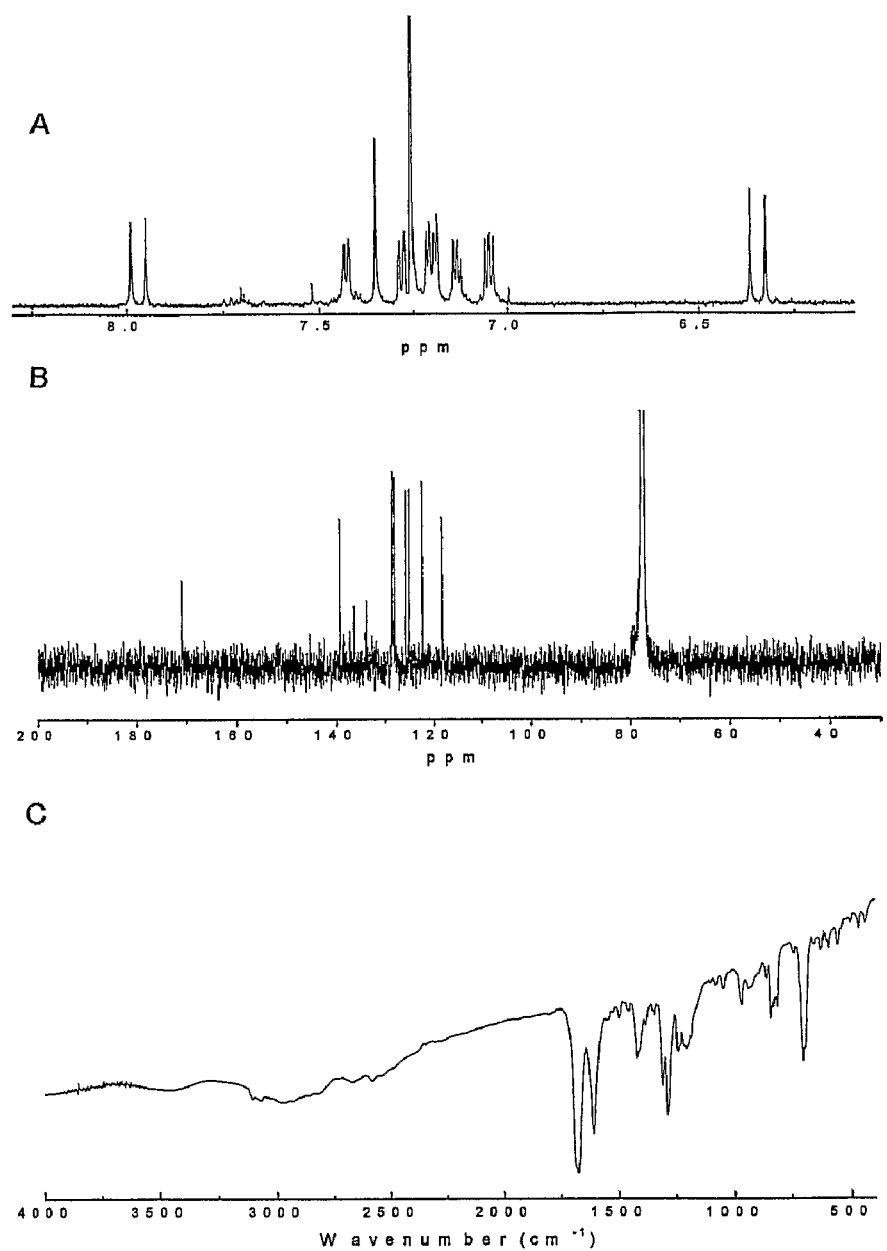
FIG. 19 (A) $^1$H NMR; (B) $^{13}$C NMR; and (C) FTIR spectra of 3-((2':2'',5'':2'''-terthiophene)-3''-yl)acrylic acid.

Compound (3) (1 g, 3 mmol) was placed in 30 mL of 1:1 (v:v) mixture of MeOH and 2 M aqueous NaOH and refluxed for 5 h, after which time the reaction mixture was allowed to cool and methanol was removed in vacuum. The aqueous solution was acidified with 5 N HCl to pH 3 and the precipitate was collected and dried in vacuum oven to give (4) as yellow powder. (0.84 g, 88%). IR; $^1$H NMR ($CDCl_3$, δ/ppm), 7.99 (d, 1H, CH=CHCOOH), 7.44 (dd, 1H, H 5'), 7.35 (s, 1H, H 4"), 7.29 (dd, 1H, H 3'), 7.22 (dd, 1H, H 5'''), 7.20 (dd, 1H, H 3'''), 7.14 (dd, 1H, H 4'), 7.06 (dd, 1H, H 4'''), 6.37 (d, 1H, CH=CHCOOH); $^{13}$C NMR (400 MHz, $CDCl_3$, δ/ppm) 170.85, 139.26, 138.44, 137.29, 136.34, 134.05, 133.78, 128.55, 128.48, 128.38, 128.04, 125.80, 125.00; 122.31, 118.22. (see, FIG. 19).

(b) Sensor Preparation

Electropolymerization

Figure 20:
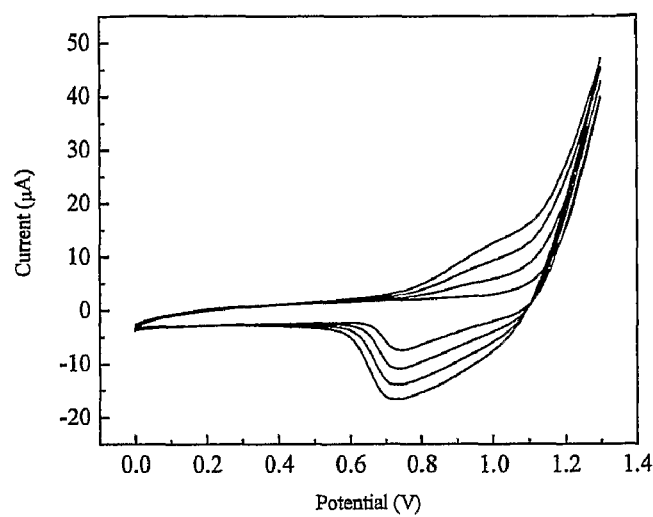
FIG. 20 Cyclic voltammograms obtained during the polymerization.
Figure 21:
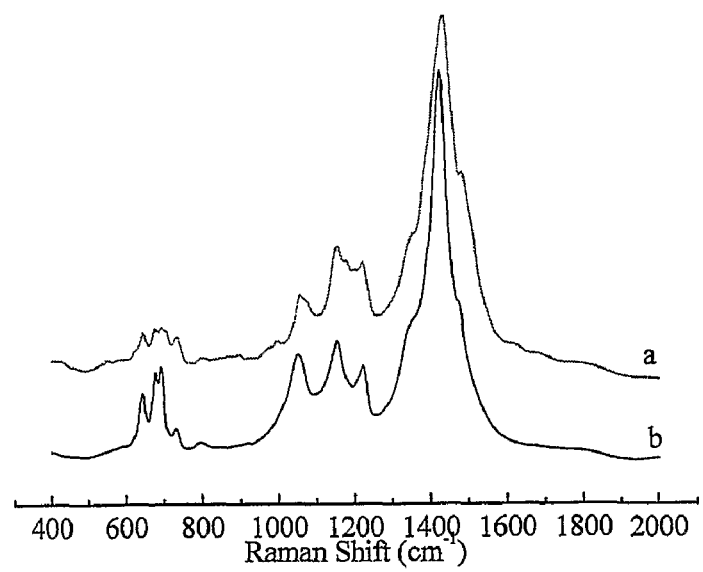
FIG. 21 Raman spectra. a: poly(TAA); b: polythiophene.

The electropolymerization was carried out by cyclic voltammetry from 0 to 1.3 V vs. Ag/AgCl at a scan rate of 100 mV/s in a standard three-electrode cell containing 0.05 M tetrabutylammonium trifluoromethanesulfonate and 0.005 M 3-((2':2",5":2'''-terthiophene)-3"-yl)acrylic acid (TAA) in $CH_2Cl_2$. The cyclic voltammograms are shown in FIG. 20. The polymer film was characterized by Raman spectroscopy, as shown in FIG. 21.

Sensor Response

To covalently attach the ODN probe 40 µl phosphate buffer (pH 5.2) containing 25 µg ODN probe and 400 nmol EDC was applied to the surface of a polymer-coated electrode, and kept at 28° C. for 10 h. Finally, the modified electrode was thoroughly washed using PBS solution (pH 7.4) in order to remove any remaining unattached ODN probes.

Figure 22:
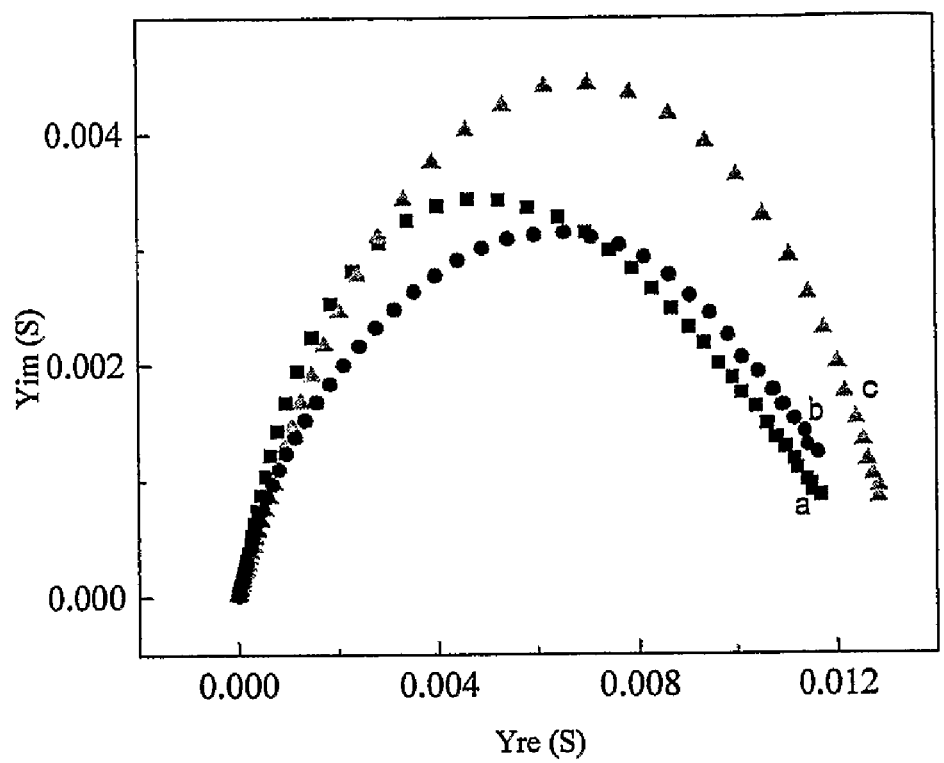
FIG. 22 Admittance spectra of poly(TAA) film (a); after immobilization of the probe (b) and after hybridization with 4.03 μM ODN target (c).

Hybridization was carried out by incubating the sensor films in PBS solution (pH 7.4) containing ODN targets for 1 h at 37.0° C. After hybridization, the electrode was washed three times using PBS solution to remove any non-hybridized ODNs. The sensor response was measured by AC impedance. The result is shown in FIG. 22.

EXAMPLE 5

Synthesis of thiophene-3-yl-acetic acid 1,3-dioxo-1, 3-dihydro-isoindol-2-yl ester (TAE)

To examine the effects of unsaturated organic linker in thiophene-based polymer film we compared electronic properties of functionalised monomer polymers formed from general formula VIII with polymers formed from TAE. TAE has a saturated linker of 2 carbon atoms.

Scheme V Synthetic route to thiophene-3-yl-acetic acid 1,3-dioxo-1,3-dihydro-isoindol-2-yl ester

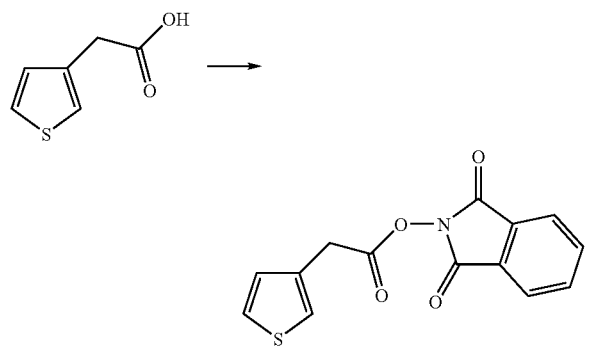

Figure 23:
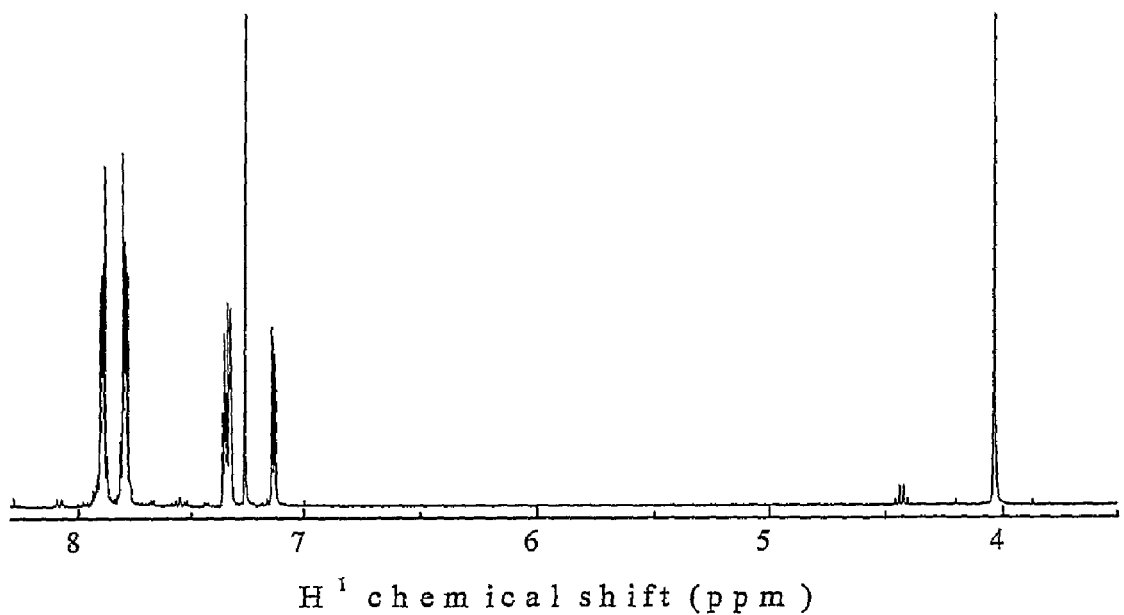
FIG. 23 $^1$H NMR spectra of thiophene-3-yl-acetic acid 1,3-dioxo-1,3-dihydro-isoindol-2-yl ester.

3-thiophene acetic acid (35 mmole, 5 g) and N-hydroxyphthalimide (NHP) (35 mmole, 6 g) was stirred in 100 mL of chloroform at room temperature. 1,3-Dicyclohexylcarbodiimide (DCC) (36 mmole, 7.5 g) was added to the reaction mixture. After complete dissolution of NHP, the reaction mixture was allowed to react for 2 h. The product was filtered and the filtrate collected. After removing solvent under vacuum, the crude product was purified by recrystallization in ether. $^1$H NMR (CDCl3) d: 7.88 (m, 2H); 7.80 (m, 2H), 7.35 (m, 1H); 7.32 (s, 1H); 7.13 (m, 1H); 4.01 (s, 2H). (see, FIG. 23).

(b) Sensor Preparation and Testing

Electrocopolymerization

The electropolymerization was carried out at constant potential at 1.65 V (vs. Ag/AgCl) in a traditional cell containing 0.1 M tetrabutylammonium trifluoromethanesulfonate, 0.1 M bithiophene and 0.1 M TAE in CH$_3$CN.

Sensor Response

To covalently attach the ODN probe, 40 μl CH$_3$CN (pH 5.2) and 10 μl of 2.5 μg/μl ODN probe was applied to the surface of a polymer-coated electrode, and kept at 28° C. for 5 h. The modified electrode was thoroughly washed using PBS solution (pH 7.4) in order to remove any remaining unattached ODN probes.

Hybridization was carried out by incubating the sensor films in PBS solution (pH 7.4) containing 4.03 μM ODN targets for 1 h at 37.0° C. After hybridization, the electrode was washed three times using PBS solution to remove any non-hybridized ODNs. The sensor responses before and after hybridization were measured by AC impedance. The result is shown in FIG. 1.

(c) Discussion of Results

To examine the effect of having an unsaturated organic linker in thiophene-based polymer film we compared the responses of the two polymer films, containing either the functionalized monomer with saturated linker (thiophene-3-yl-acetic acid 1,3-dioxo-1,3-dihydro-isoindol-2-yl ester) (TAE) or functionalized monomer with unsaturated linker (3-((2':2″,5″:2‴-terthiophene)-3″-yl)acrylic acid) (TAA).

Figure 24:
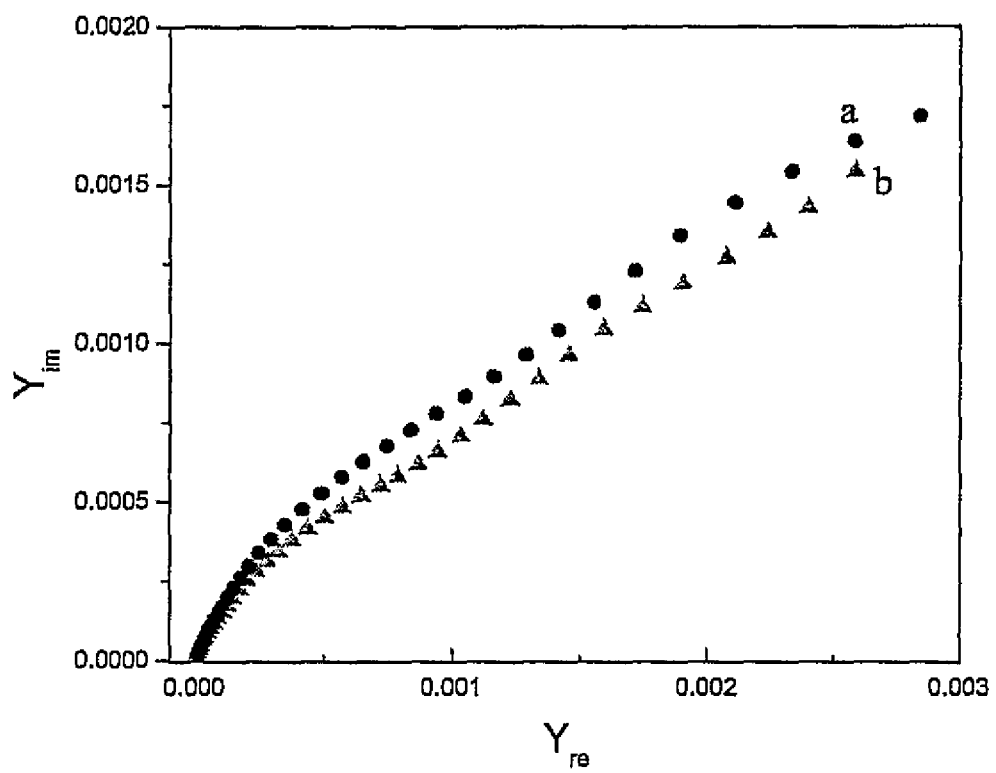
FIG. 24 Admittance spectra of poly(TAE-co-bithiophene)-ODN film before (a) and after (b) hybridization with 4.03 μM ODN target.

Comparing AC admittance spectra of poly(TAA) (FIG. 22) and poly(TAE-co-bithiophene) films (FIG. 24), functionalized with ODN probes, before and after hybridization event, one can see that the film poly(TAA) film showed much higher response. In fact, the poly(TAE) response was almost within the experimental error. Although this comparison should be taken with some reservation due to the difference in the length of linkers (3-carbon chain in TAA vs. 2-carbon chain for TAE) and somewhat different composition of the polymers, it is still considered to be a good indication of the improved effect of the unsaturated linker in thiophene-based polymers on the sensor response.

The obtained response with poly(TAA) film is opposite to the responses obtained with pyrrole-based (co)polymers and in agreement with published data on thiophene-based sensor films that have saturated side chains (T.-Y. Lee, Y.-B. Shim, Analytical Chemistry 2001, 73, 5629; J. Cha, J. I. Han, Y. Choi, D. S. Yoon, K. W. Oh, G. Lim, Biosensors & Bioelectronics 2003, 18, 1241).

Several explanations have been proposed in those references. We believe that the different response in thiophene-based films presented in this document may be due to cation-movement (opposite to anion-movement in polypyrrole films) to balance the charges on the polymer chains. In this case, the increase in electron density, due to the probe-target complex, would facilitate the cation-movement and increase the admittance, as seen in FIG. 22. The exact mechanism of the sensor responses are currently being studied in our laboratory.

While in the foregoing description there has been made reference to specific components or integers of the invention having known equivalents then such equivalents are herein incorporated as if individually set forth.

Although this invention has been described by way of example only and with reference to possible embodiments thereof it is to be understood that modifications or improvements may be made without departing from the scope or spirit of the invention.

What we claim is:

1. A conducting polymer including a conducting linker to connect a probe to the polymer, the linker including a conjugated organic chain and/or an aromatic ring, wherein conjugation is maintained along the length of the linker and between the linker and the conducting polymer.

2. A conducting polymer according to claim 1, wherein the linker is adapted to locate the probe at a predetermined distance from remaining portions of the polymer thereby optimising sensory properties of the probe.

3. A conducting polymer according to claim 1, wherein the linker has a predetermined range of orientations brought about by unsaturated bonds.

4. A conducting polymer according to claim 1, wherein the linker is of general formula I, II, III, or IV:

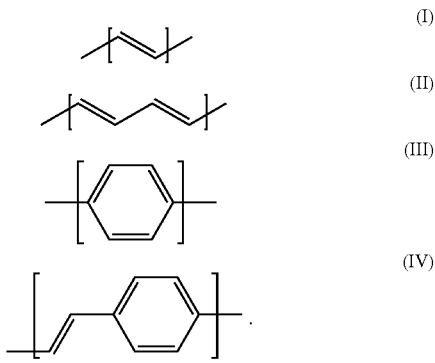

5. A conducting polymer according to claim 1, wherein the linker extends from at least one monomer of the polymer.

6. A conducting polymer according to claim 5, wherein the polymer is a polypyrrole, polythiophene, polyaniline, poly(p-phenylene vinylene), or poly(p-phenylene) polymer.

7. A conducting polymer including a conducting linker to connect a probe to the polymer, the linker including a conjugated organic chain and/or an aromatic ring and extending from a functionalized monomer of general formula V:

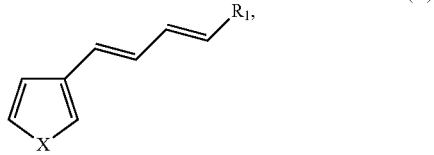

(V)

wherein X is N, S or O, $R_1$ is —$NH_2$, —$CO_2H$, —COH, —OH, or N-hydroxyphthalimide, and conjugation is maintained along the length of the linker and between the linker and the conducting polymer.

8. A functionalized monomer according to claim 7, wherein one preferred form of the compound is 5-(1 H-pyrrol-3-yl)2,4-pentadienoic acid (PPDA).

9. A conducting polymer including at least one functionalized monomer of general formula VI:

(VI)

wherein X is N, S, or O, and $R_2$ includes a conjugated organic chain and/or an aromatic ring, wherein the conjugated chain or aromatic ring is adapted to engage with a probe, and conjugation is maintained along the length of $R_2$ and between $R_2$ and the five-member ring of the functionalized monomer of formula VI.

10. A conducting polymer according to claim 9, wherein $R_2$ is of general formula I to IV and provides a functional group at the free end.

11. A conducting polymer according to claim 10, wherein the functional group is —$NH_2$, —$CO_2H$, —COH, —OH, or N-hydroxyphthalimide.

12. A conducting polymer according to claim 9, wherein the conducting polymer is formed from the polymerisation or co-polymerisation of the functionalized monomer.

13. A conducting polymer according to claim 9, wherein the conducting polymer is formed from co-polymerisation of the functionalized monomer with an unsubstituted or non-functionalized monomer.

14. A conducting polymer according to claim 12, wherein the co-polymerisation involves a ratio of non-functionalized to functionalized monomers of 10000:1 to 1:1.

15. A conducting polymer according to claim 9, wherein the unsubstituted or non-functionalized monomer is pyrrole or thiophene.

16. A method of preparing a conducting polymer, the method comprising the step of:

homopolymerisation or copolymerisation with a functionalized monomer of general formula VII:

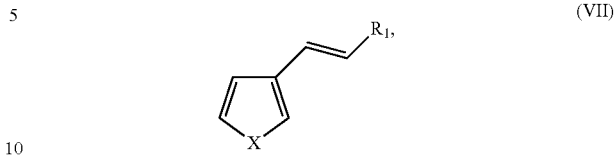

(VII)

wherein X is N, S, or O, and $R_1$ is a functional group.

17. The method according to claim 16, wherein the functional group is —$NH_2$, —$CO_2H$, —COH, —OH, or N-hydroxyphthalimide.

18. A functionalized monomer of general formula VIII:

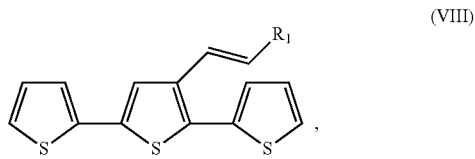

(VIII)

wherein $R_1$ is —$NH_2$, —$CO_2H$, —COH, —OH, or N-hydroxyphthalimide.

19. A method of preparing a conducting polymer, the method comprising the step of:
homopolymerisation or copolymerisation with a functionalized monomer of general formulas V, VII, or VIII.

20. The method according to claim 19, wherein the conducting polymer includes functionalized and non-functionalized monomers.

21. The method according to claim 20, wherein the functionalized monomers include copolymerised functionalized monomers.

22. The method according to claim 21, wherein the ratio of non-functionalized monomers to copolymerised functionalized monomers is between about 80:1 and about 1:1.

23. A conducting linker connecting a probe to a conducting polymer, the linker including a conjugated organic chain, wherein conjugation is maintained along the length of the linker and between the linker and the conducting polymer.

24. A method of reducing charge transfer resistance between a conducting polymer and a probe, the method including the steps of connecting the conducting polymer to the probe via a linker constructed of a conjugated organic chain and/or an aromatic ring, wherein conjugation is maintained along the length of the linker and between the linker and the conducting polymer.

25. The method of claim 24, wherein the linker is selected from any one of the groups of general formula I, II, III, or IV.

26. A method of preparing a conducting polymer of claim 1 including the steps of carrying out polymerisation of polymer monomers in a solvent of $LiClO_4$ in acetonitrile or propylene carbonate.

* * * * *

UNITED STATES PATENT AND TRADEMARK OFFICE
CERTIFICATE OF CORRECTION

PATENT NO. : 8,378,058 B2
APPLICATION NO. : 12/063221
DATED : February 19, 2013
INVENTOR(S) : Jadranka Travas-Sejdic et al.

It is certified that error appears in the above-identified patent and that said Letters Patent is hereby corrected as shown below:

On the title page, item (75) should read

-- (75)  Inventors:  Jadranka Travas-Sejdic, Auckland (NZ); Christian Soeller, Auckland (NZ); Hui Peng, Auckland (NZ); Vittorio Caprio, Auckland Central (NZ); Ralph Cooney, Auckland, (NZ) --

Signed and Sealed this
Twenty-fifth Day of June, 2013

Teresa Stanek Rea
*Acting Director of the United States Patent and Trademark Office*